(12) United States Patent
Albro et al.

(10) Patent No.: US 10,074,059 B1
(45) Date of Patent: Sep. 11, 2018

(54) MEDICAL TREATMENT APPLICATION FOR OPTIMIZING MEDICAL PATIENT VISITS BASED ON KNOWN PREFERENCES AND OTHER SELECTION CRITERIA

(71) Applicant: West Corporation, Omaha, NE (US)

(72) Inventors: Douglas R. Albro, Mobile, AL (US); Kenneth A. Darby, Papillion, NE (US); Robert J. Dudzinski, Omaha, NE (US); Michael J. Masching, Omaha, NE (US); Pamela Ann Mortenson, Blair, NE (US); Bruce Pollock, Omaha, NE (US); Hendryanto Rilantono, Omaha, NE (US)

(73) Assignee: West Corporation, Omaha, NE (US)

( * ) Notice: Subject to any disclaimer, the term of this patent is extended or adjusted under 35 U.S.C. 154(b) by 1098 days.

(21) Appl. No.: 14/283,371

(22) Filed: May 21, 2014

(51) Int. Cl.
*G06Q 10/06* (2012.01)
*G06Q 30/02* (2012.01)
*G16H 20/00* (2018.01)

(52) U.S. Cl.
CPC . *G06Q 10/063116* (2013.01); *G06Q 10/0631* (2013.01); *G06Q 30/0282* (2013.01); *G16H 20/00* (2018.01)

(58) Field of Classification Search
CPC .............. G06Q 50/22; G06Q 30/0282; G06Q 10/0631; G06Q 10/063116; G16H 20/00
See application file for complete search history.

(56) References Cited

U.S. PATENT DOCUMENTS

| 8,271,295 | B1 * | 9/2012 | Miller | G06F 19/327 340/531 |
| 2009/0138283 | A1 * | 5/2009 | Brown | G06Q 10/109 705/3 |

* cited by examiner

*Primary Examiner* — Minnah L Seoh
(74) *Attorney, Agent, or Firm* — Raffi Gostanian

(57) ABSTRACT

Medical services are offered by various facilities near a patient's residence. The number of facility optimization procedures continues to grow and the patients and facilities can now apply new logic processes and patient profiling, etc., to maximize efficiency and budgetary concerns. One example method of operation provides receiving a request to schedule a medical care visit at a medical facility and identifying a user account associated with the request and the user's medical history. The method may also include identifying the user account as having a delinquent compliance score, and scheduling the medical care visit in a delinquent appointment time slot.

14 Claims, 28 Drawing Sheets

MEDICAL TREATMENT APPLICATION FOR OPTIMIZING MEDICAL PATIENT VISITS BASED ON KNOWN PREFERENCES AND OTHER SELECTION CRITERIA

CROSS-REFERENCE TO RELATED APPLICATION

This application incorporates by reference U.S. patent application Ser. Nos. 14/283,341; 14/283,418; 14/283,424; 14/283,432; 14/283,437; 14/283,442; 14/283,451; 14/283,460; and 14/283,467; the entire contents of each of which is hereby incorporated by reference.

TECHNICAL FIELD OF THE APPLICATION

This application relates to assisting patients with continuing health care management via a computer-based application, and more specifically to optimizing patient appointments, insurance payment options, medical facility treatment and other aspects of medical patient interactions.

BACKGROUND OF THE APPLICATION

The majority of health care providers offer services, prescriptions, treatment regiments, advice, etc., to patients on a daily basis. As patients require access to doctors, prescription medicine, hospitals, etc., the number of options available for the patient may be numerous.

Health care systems in place today in the United States demand health care coverage but often provide different options to insured users. Most options are unknown to the users, however, different users have different goals when seeking medical treatment. For example, a user may have a primary goal of obtaining the best health care possible and may rely on reputation above all other considerations when seeking health care facilities and treatment. Another very busy user may seek only the closest option as time is of the essence to that user at all times. Still yet another user may want the health insurance reimbursements to be optimal at all times so no unnecessary costs are incurred for any type of medical treatment.

Regardless of the user's interests or goals when seeking medical treatment, the options for treatment are numerous and can often lead to overwhelming decisions for otherwise sensitive concerns related to the well-being of oneself or loved ones. Having options is always the best approach to alleviate stressful situations and especially when the options are tailored to a person's goals and preferences.

SUMMARY OF THE APPLICATION

One example embodiment may include a method of receiving a request to schedule a medical care visit at a medical facility, identifying a user associated with the request and the user's medical history, calculating a medical facility placement score based on a plurality of user medical history parameters associated with the user's medical history, and scheduling the medical care visit at a medical facility that provides the largest medical facility placement score.

Another example embodiment may include an apparatus that includes a receiver configured to receive a request to schedule a medical care visit at a medical facility, and a processor configured to identify a user associated with the request and the user's medical history, calculate a medical facility placement score based on a plurality of user medical history parameters associated with the user's medical history, and schedule the medical care visit at a medical facility that provides the largest medical facility placement score.

Yet another example embodiment may include a method that includes identifying a plurality of feedback messages associated with a particular medical facility, parsing the feedback messages to identify negative feedback associated with the plurality of feedback messages, notifying the medical facility of the negative feedback, and transmitting a plurality of suggestions to increase productivity and reduce subsequent negative feedback messages for subsequent patient visits to the medical facility.

Still another example embodiment may include an apparatus that includes a processor configured to identify a plurality of feedback messages associated with a particular medical facility, parse the feedback messages to identify negative feedback associated with the plurality of feedback messages, notify the medical facility of the negative feedback, and a transmitter configured to transmit a plurality of suggestions to increase productivity and reduce subsequent negative feedback messages for subsequent patient visits to the medical facility.

Yet another example embodiment may include a method that includes receiving a request to schedule a medical care visit at a medical facility, identifying a user account associated with the request and the user's medical history, identifying the user account as having a delinquent compliance score, and scheduling the medical care visit in a delinquent appointment time slot.

Still yet another example embodiment may include an apparatus that includes a receiver configured to receive a request to schedule a medical care visit at a medical facility, and a processor configured to identify a user account associated with the request and the user's medical history, identify the user account as having a delinquent compliance score, and schedule the medical care visit in a delinquent appointment time slot.

Further still another example embodiment may include a method that includes receiving a request to schedule a medical care visit at a medical facility from a user device associated with a user account, scheduling the first appointment for a first appointment time on an appointment list, identifying an open appointment time in the appointment list for the same day, and transmitting a notification to at least one user device associated with at least one user account that is eligible for an appointment rescheduling event, and receiving a response message confirming a schedule change responsive to the notification being transmitted the user device.

Yet another example embodiment may include an apparatus that includes a receiver configured to receive a request to schedule a medical care visit at a medical facility from a user device associated with a user account, a processor configured to schedule the first appointment for a first appointment time on an appointment list, identify an open appointment time in the appointment list for the same day, and a transmitter configured to transmit a notification to at least one user device associated with at least one user account that is eligible for an appointment rescheduling event, and wherein the receiver is further configured to receive a response message confirming a schedule change responsive to the notification being transmitted the user device.

Still another example embodiment may include a method that includes identifying an appointment scheduled for a medical treatment facility for a registered patient, retrieving patient history information responsive to identifying the appointment scheduled, applying at least one insurance policy to the appointment scheduled, and processing a set of rules associated with the at least one insurance policy and comparing the set of rules to at least one present billing event associated with the appointment scheduled.

Yet another example embodiment may include an apparatus that includes a processor configured to identify an appointment scheduled for a medical treatment facility for a registered patient, retrieve patient history information responsive to identifying the appointment scheduled, apply at least one insurance policy to the appointment scheduled, and process a set of rules associated with the at least one insurance policy and comparing the set of rules to at least one present billing event associated with the appointment scheduled.

Still another example embodiment may include a method that includes receiving patient diagnostic measurements associated with a patient on a periodic basis from a patient computing device, compiling the patient diagnostic measurements as a medical report stored in memory, processing the medical report to identify a present course of treatment for the patient, and transmitting the medical report to an interested party.

Yet another example embodiment may include an apparatus that includes a receiver configured to receive patient diagnostic measurements associated with a patient on a periodic basis from a patient computing device, a processor configured to compile the patient diagnostic measurements as a medical report stored in memory, process the medical report to identify a present course of treatment for the patient, and a transmitter configured to transmit the medical report to an interested party.

Still yet further another example embodiment may include a method that includes storing patient information in a data file of a user computing device, receiving a request for patient information, identifying a present course of treatment for the patient, comparing the present course of treatment to the patient information, and transmitting a response indicating at least one prohibitive action.

Yet another example embodiment may include an apparatus that includes a memory configured to store patient information in a data file of a user computing device, a receiver configured to receive a request for patient information, a processor configured to identify a present course of treatment for the patient, and compare the present course of treatment to the patient information, and a transmitter configured to transmit a response indicating at least one prohibitive action.

DETAILED DESCRIPTION OF THE APPLICATION

It will be readily understood that the components of the present application, as generally described and illustrated in the figures herein, may be arranged and designed in a wide variety of different configurations. Thus, the following detailed description of the embodiments of a method, apparatus, and system, as represented in the attached figures, is not intended to limit the scope of the application as claimed, but is merely representative of selected embodiments of the application.

The features, structures, or characteristics of the application described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present application. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments of the present application, the application may be applied to many types of network data, such as, packet, frame, datagram, etc. For purposes of this application, the term "message" also includes packet, frame, datagram, and any equivalents thereof. Furthermore, while certain types of messages and signaling are depicted in exemplary embodiments of the application, the application is not limited to a certain type of message, and the application is not limited to a certain type of signaling.

Figure 1:
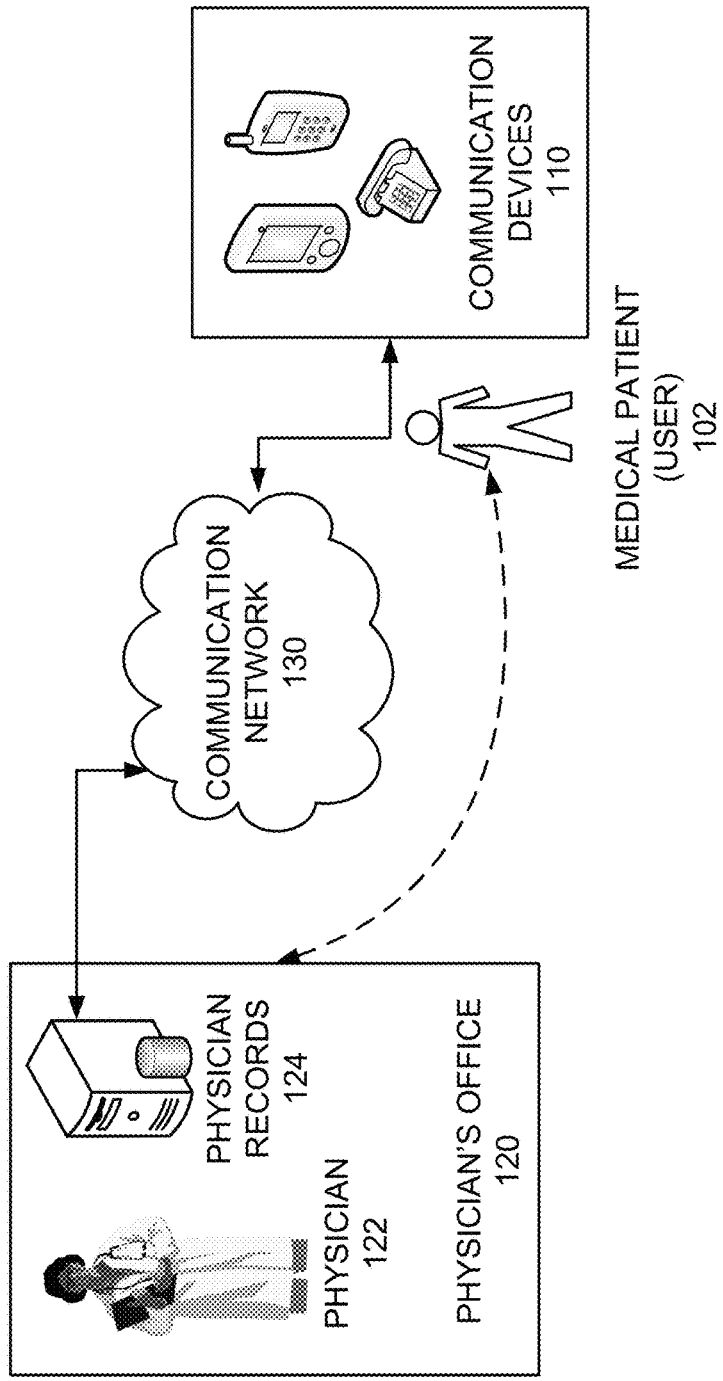
FIG. 1 illustrates a conventional prior art logic diagram of a user's interactions with a health care provider.

FIG. 1 illustrates a conventional prior art logic diagram of a network model of a user's interactions with a health care provider communication system. Referring to FIG. 1, in the past the network configuration 100 would include a medical patient or user 102 establishing a doctor's appointment with a physician's office 120 including a physician records database 124 and a live physician 122, via a phone interaction or an online setup procedure. The user 110 would have a health insurance plan, a past medical record established by the health insurance provider, a pharmacy record stored in a pharmacy computing system accessible via a local pharmacy and/or a physician electronic medical record, etc. The user may select a communication device 110 and communicate with the physician's office 120 over a communication network 130. The patient 102 can call the physician office directly to setup an appointment for any purpose. However, the information available to the patient is limited to what he or she has learned from previous office visits, bills, procedures, etc.

Figure 2:
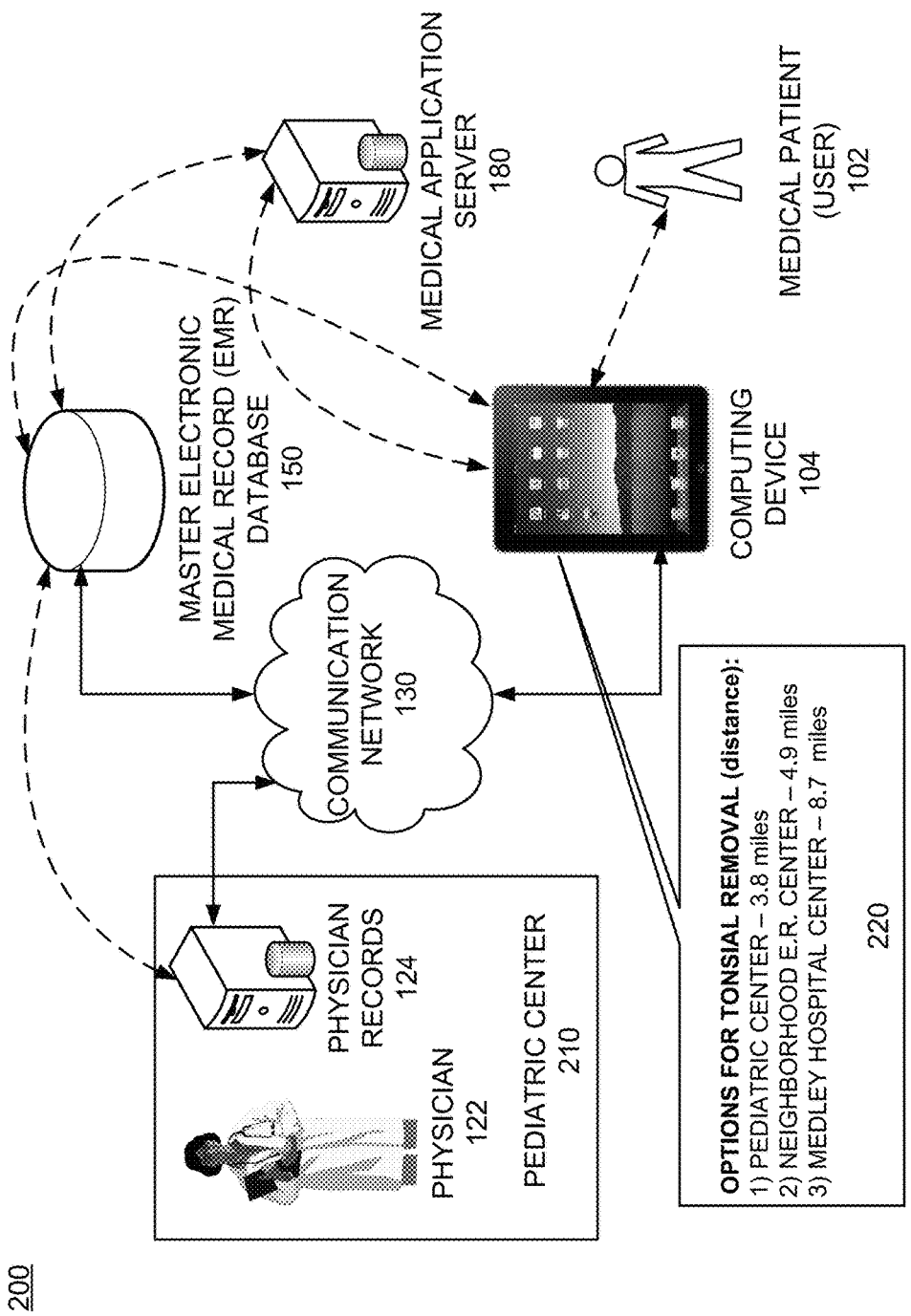
FIG. 2 illustrates an example logic diagram of a user's interactions with a health care service application, according to an example embodiment of the present application.

FIG. 2 illustrates an example logic diagram of a user's interactions with a health care service application, according to an example embodiment of the present application. Referring to FIG. 2, the network 200 includes additional features and network elements, such as a computing device (e.g., smartphone, computer, tablet, etc.), a master electronic medical record (EMR) database 150, and a medical application server 180. The user 102 may attempt to setup an appointment via a medical assistant application operating on the smartphone or tablet device 104. The application may communicate with a medical application server 180 that stores a user profile which may be associated with the electronic medical record 150. The user may have a name, address and other basic information along with more customized and useful information, such as insurance information, medical insurance coverage type, preferences, history of medical treatment, medical goals (e.g., checkup this year, colonoscopy this year, etc.).

In the example of FIG. 2, the user or patient's goals may be setup to first return results regarding distance. For example the user may have entered a number of different preferences, however, the initial setup may include medical treatment facility locations as the top priority, and thus the first set of results when the patient 102 enters "tonsillectomy" into the medical assistant application may yield results 220 of qualifying facilities that offers such services, are within the coverage of the user's health plan and which are closest to the user's present location or address 102. This example is merely exemplary in nature as various different criteria and priorities may yield different results depending on the user's customized preferences and query submissions.

According to one example embodiment, the user medical assistant application may provide logic and processing for a user health plan (qualifying/non-qualifying services), a facility location (predetermined radius), a facility reputation (scale of 1-10), a facility cost structure (most affordable, less affordable, expensive), physician rankings, etc. Each of these variables may be setup numerically and provide individual weighted results or a combined weighted function. Additional criteria may be applied to create a set of results listed in a ranked tabular format for optimal user satisfaction. For example, the user may be interested in identifying copay costs, deductibles for the present year, scheduling likelihood of success, specific procedure accommodations, etc.

In general, a patient may be likely to prefer the closest facility and the cheapest cost. However, some patients are more interested in reputation and the doctor(s) reputations prior to scheduling any type of procedure. A user may setup a ranking, such as #1 priority—'cost', #2 priority—'location', #3 priority—'facility reputation', #4 priority—'facility availability', #5 priority—'physician reputations'. In this example, the medical facility placement function (FPF) may provide FPF=cost(W5)+location(W4)+facility reputation(W3)+facility availability(W2)+physician reputation(W1). The value of each weight may be '1' and the weight applied may be 5, 4, 3, 2, 1, etc. multiplied by that variable. The patient may enter a scheduling request for a particular appointment, such as a 'patient physical'. This type of procedure is performed by just about all types of facilities with primary care physicians or similar types of physicians. In this example, certain thresholds may be used to include the above-noted preferences or disregard them accordingly. For example, the cost variable may have a particular threshold above which the results will be set to '0' which will hurt that facilities overall weighted function and placement function. If the facility is too expensive the first and most important weight of cost will be '0' and the score will be largely affected, and thus the facility may rank low in a tabular output format returned to the user.

Figure 3A:
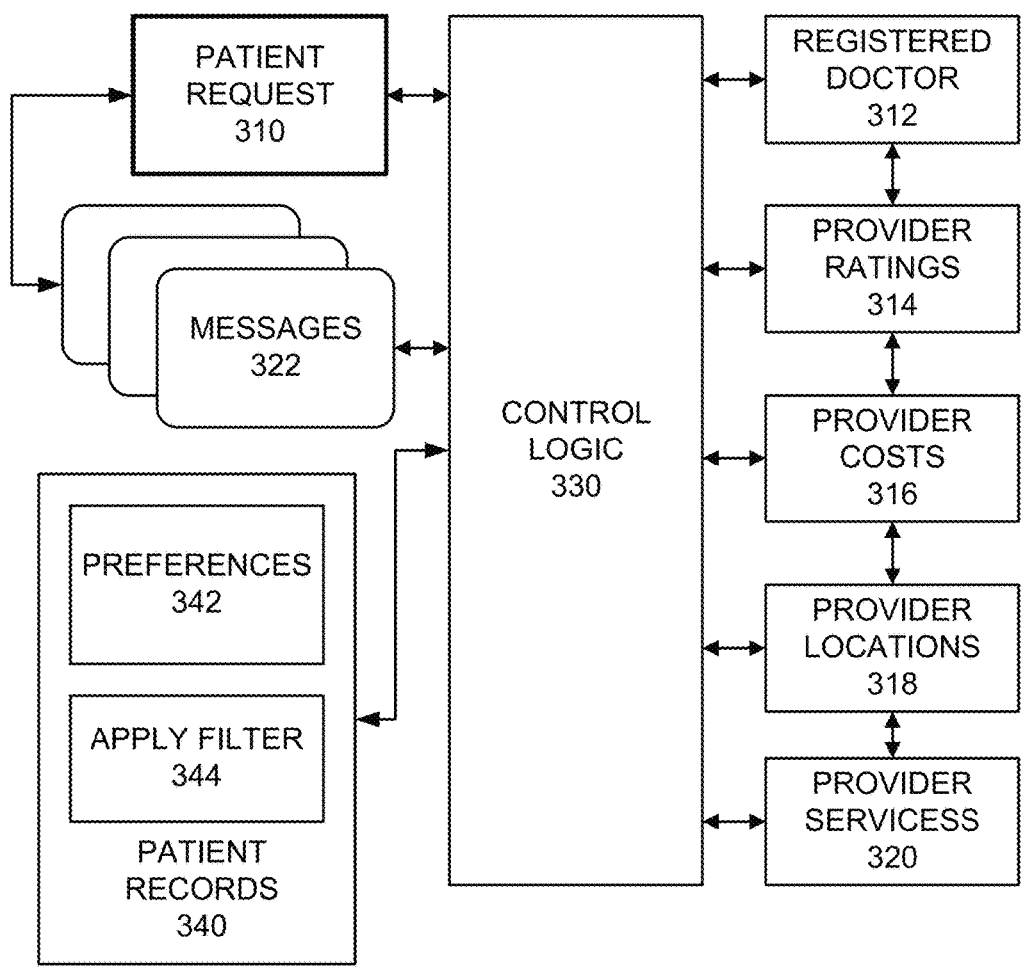
FIG. 3A illustrates an example logic diagram of a patient health care application for identifying patient treatment facilities according to example embodiments of the present application.

FIG. 3A illustrates an example logic diagram of a patient health care application for identifying patient treatment facilities according to example embodiments of the present application. Referring to FIG. 3A, the control logic processor 330 and corresponding medical assistant application may provide an initial patient request 310 for a medical service. The request may include a treatment procedure (i.e., diabetes, tonsillectomy, colonoscopy, physical, etc.). The input may be simple and only request a single service or treatment. However, the logic 330 may apply various data points including the registered doctor location 312, the provider ratings 314, the provider costs 316, the provider locations 318 and the provider services 320 to identify if the facility is suitable to satisfy the user request. The user's preferences 342 are known and stored in memory and can be retrieved and applied to the fixed variables noted above. A filter 344 may be used to ensure the user's preferences are being applied to the processing module 330 to limit the results generated. The filter and the preferences may be stored in a patient record 340. Once the results are obtained, a set of messages 322 may be created to email, text message, and/or call, the user to confirm the results/options and offer an option to setup an appointment.

Additionally, the results may be offered as an ordered list with the most relevant option at the top. The results may also be offered with a grid of information, such as copay costs facility #1 $15, facility #2 $20, distance facility #1 1 mile, facility #2 3 miles, etc. The user can then quickly ascertain the variables which are most important at the present time (i.e., distance, cost, reputation, etc.) and whether such information will be the basis for a selection and appointment setup.

Figure 3B:
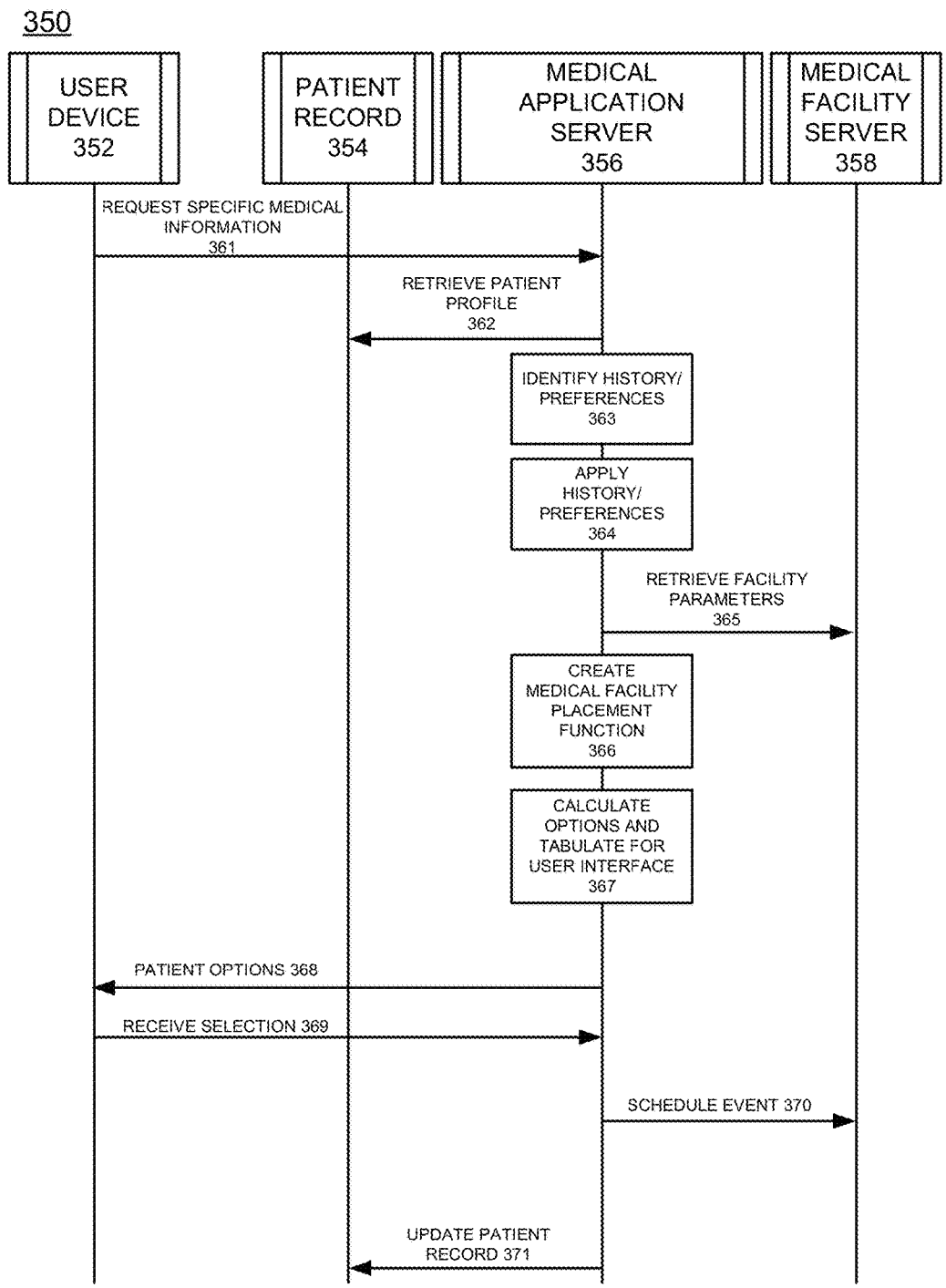
FIG. 3B illustrates a system communication diagram of an example communication process for identifying patient treatment facilities according to example embodiments.

FIG. 3B illustrates a system communication diagram of an example communication process for identifying patient treatment facilities according to example embodiments. Referring to FIG. 3B, the diagram 350 includes communication among a user device 352, a patient record file, data source, etc. 354, a medical application server 356 which hosts the application on the user device 352 and a medical facility server 358 which is operated by the facility to maintain patient information, appointments and other facility specific information. In operation, the user device would submit a request for a certain medical treatment or related information 361. The request would be received at the application server 356 which can then retrieve the patient profile 362 and identify the user history, such as previous medical conditions, previous appointments, previous outcomes, feedback, etc. and also the user's preferences 363.

The preferences may be applied to a logic processing module that may identify various matches between the preferences and the information available for the medical facilities. The facility server 358 may offer certain updates to the information including parameters 365, such as present physicians and their rankings, scheduling, procedures, insurance types being accepted. The application server 356 can then setup a facility placement function 366 based on the available data, the user preferences and other data. The function may produce a list of facilities and their corresponding order, relevancy and other information that can alleviate the user's decision to select a facility and schedule an appointment.

Figure 3C:
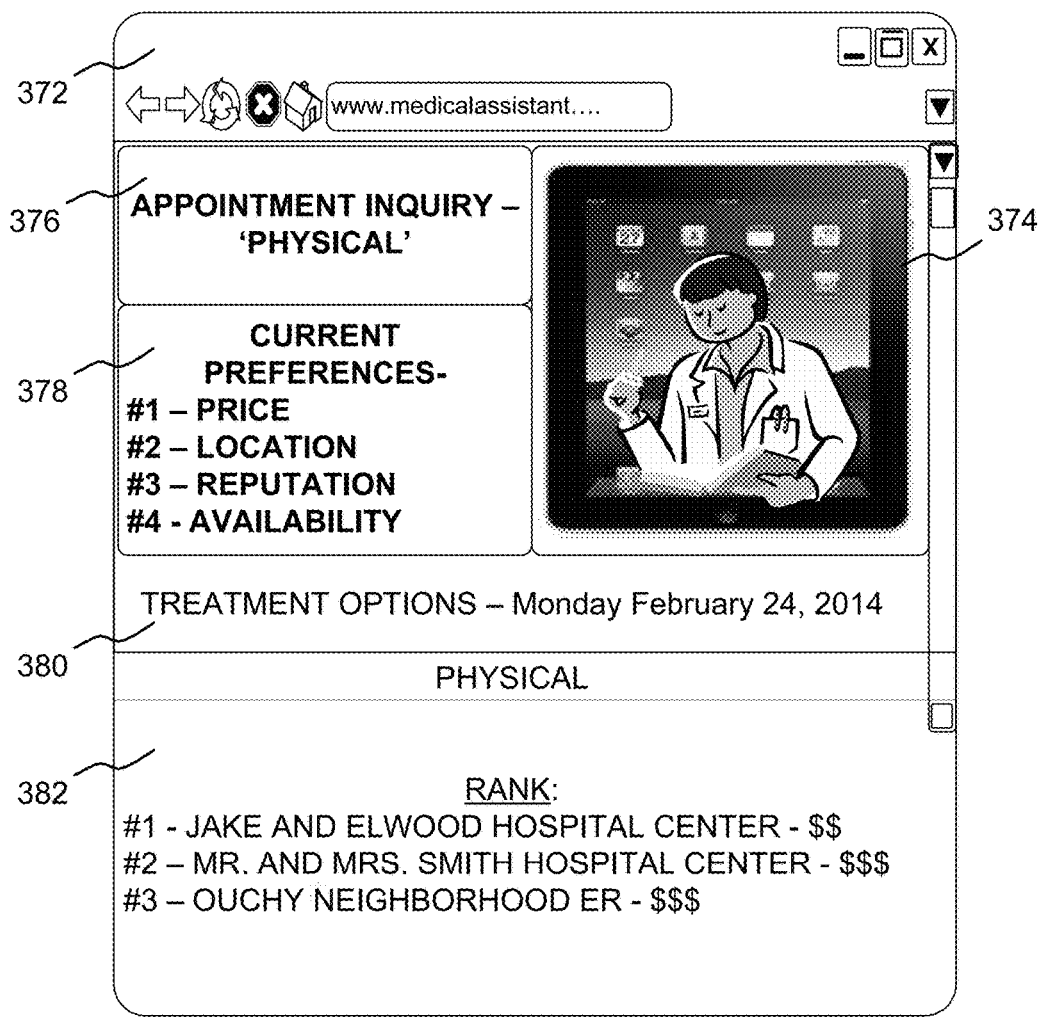
FIG. 3C illustrates an example user interface of a patient receiving feedback from the medical assistant application based on the predefined calculation metrics.

FIG. 3C illustrates an example user interface of a patient receiving feedback from the medical assistant application based on the predefined calculation metrics. Referring to FIG. 3C, the user interface 370 includes a browser interface with a website address header 372 indicated the address of the assistant application. The interface may be an application on a computing device or a web-based portal. The user's inquiry is illustrated as an input parameter 376 and a snapshot of the user device 374 which may include a talking nurse avatar or assistant that may show illustrations, such as educational videos, appointment literature for a particular procedure, and/or a photo or video of the facilities, maps, etc. The user's preferences are shown at 378 as being ordered by priority and which may have corresponding weights to ensure the results are processed according to the user's preferences. The treatment options 380 are also provided with a current date so the user is able to ascertain the results topic and feedback along with the tallied results 382, weighted and displayed in order according to the user preferences. As may be observed, the results 382 included a price index ($, $$, $$$, $$$$, etc.) to indicate which facility costs more for that particular service including discounts applied for insurance, etc.

Users may rank facilities based on a level of customer service care within the facility as well as the experience for pre-visitation, appointment setup, post-appointment follow-up, etc. Also, certain attributes could be ranked as well, such as facility cleanliness, staff politeness, professionalism, attention to detail, quality of care of physicians or other medical personnel. User preferences for application to a facility selection operation may include hours of operation, distance, available staff, service quality rating, price, accessibility, review information, insurance relationships, services offered, languages spoken, location to public transportation, handicap accessibility, work shift schedule, transportation options, etc. In one example, a user may be seeking immediate medical assistance at 3 am but may still desire to know which has the best quality service ranking and the lowest copay option. The user may enter such information into the application as first and second priority criteria before receiving a list of options ranked in the order of the criteria entered.

Figure 3D:
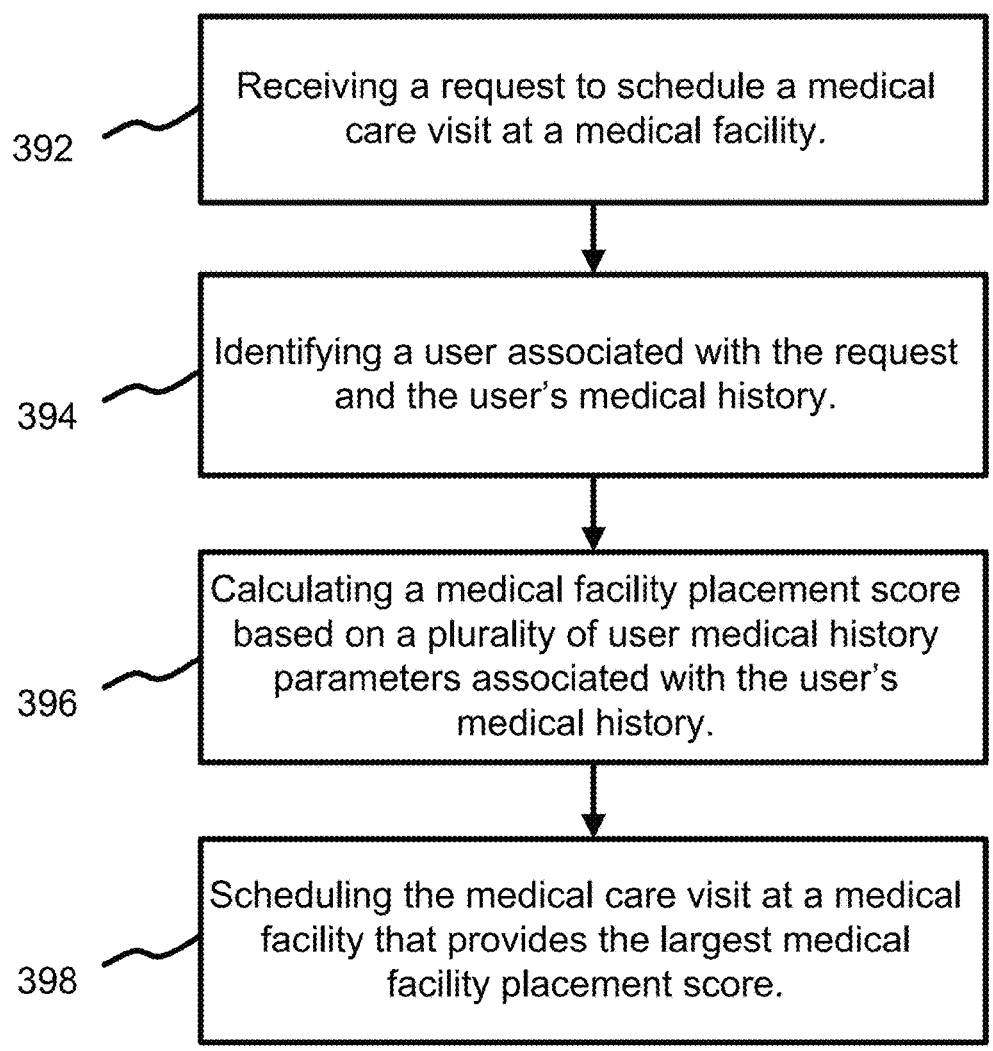
FIG. 3D illustrates an example flow diagram of an example method of operation according to example embodiments.

FIG. 3D illustrates an example flow diagram of an example method of operation. Referring to FIG. 3D, the flow diagram 390 includes receiving a request to schedule a medical care visit at a medical facility from a user device at operation 392. The request may specify a type of treatment, a preference parameter(s), a time, a location, an age range of the patient, and other information useful to generate results. Another operation may include identifying a user associated with the request and the user's medical history at operation 394. The history may be part of a patient medical record and a history of treatments, conditions, insurance information, previously consulted physicians. The input from the request, the information retrieved and other data may be used as the basis for calculating a medical facility placement function based on a number of user medical history parameters associated with the user's medical history at operation 396.

Once the results are shared, the patient can either select an appointment and a facility or the application may perform the appointment selection automatically and schedule the medical care visit at the medical facility that provides a largest medical facility placement score based on the calculation at operation 398. Continuing with the same example, the method may provide identifying a number of medical facilities that may be accommodating to the user based on the medical history parameters and preferences, and offering the medical facility with the largest medical facility placement score.

According to another example embodiment, a medical facility may receive feedback regarding its current operating status via an automated platform designed for continued process optimization. For instance, a facility may be ranked or identified via an automated survey created and provided to the user automatically from the medical assistant application. After visiting the facility, the user or patient may receive a survey to rank the facility, the experience with the physician, and to share his or her overall experience. Such information can be the basis for an automated facility improvement procedure.

Figure 4A:
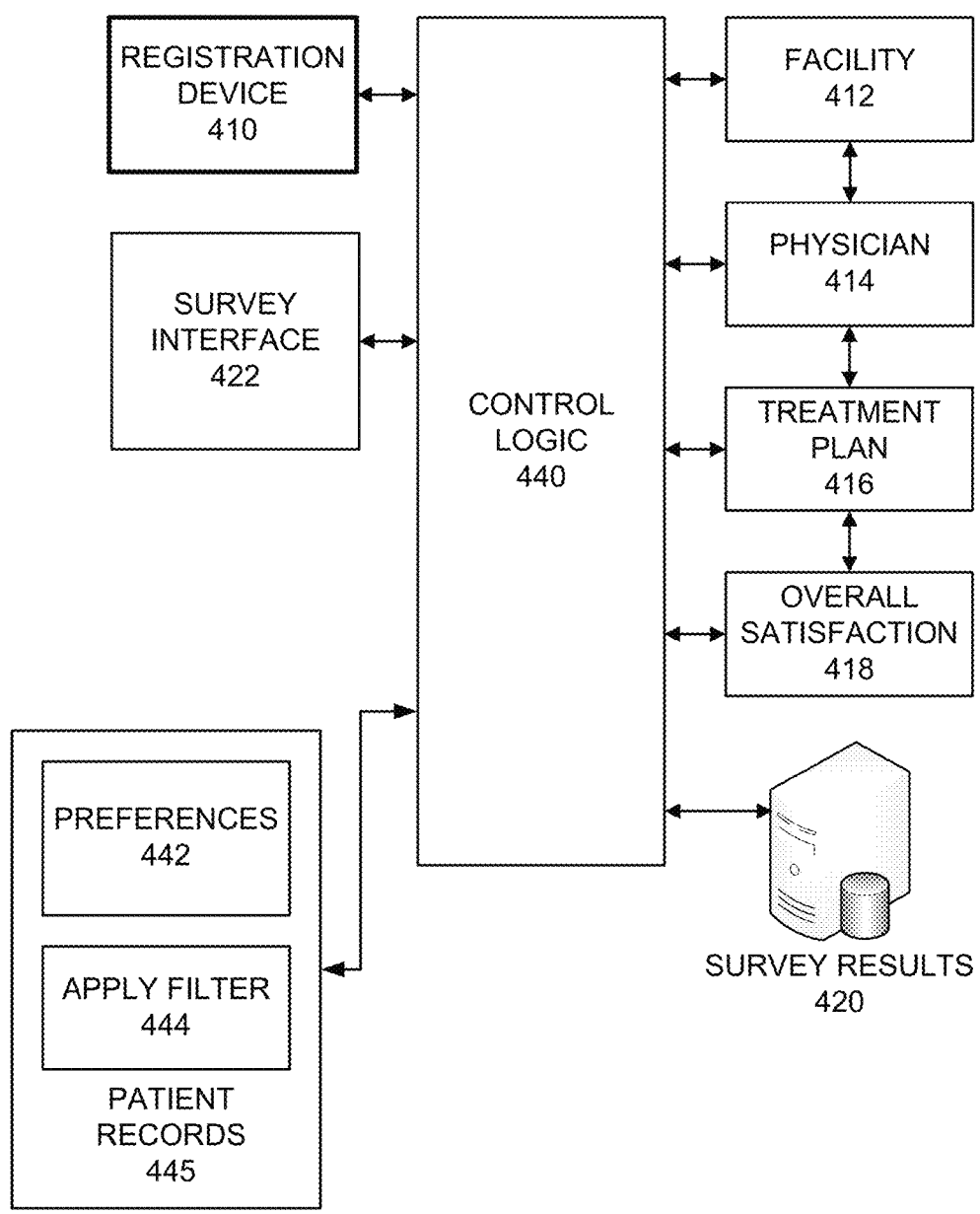
FIG. 4A illustrates an example logic diagram of a patient health care application for optimizing medical treatment facilities according to example embodiments of the present application.

FIG. 4A illustrates an example logic diagram of a user survey feedback configuration according to example embodiments. Referring to FIG. 4A, the logic diagram 400 includes a control logic processor 440 which receives input from registration device 410, such as a user computing device and provides a user survey interface 422 for the user to submit survey input to the questions being asked. The user preferences 442 and a corresponding filter 444 may be used to identify the user and further enhance the survey experience. For example, if the user has a patient record 445 with preferences 442 that include price and location as the higher priority preferences, then the survey may dynamically modify the questions to focus on the user's primary and secondary interests while omitting other less relevant questions. The survey may begin with simple questions and ask more specific questions that are related to the user's experience at a particular medical facility. The facility 412 may be identified from memory as having a number of corresponding questions which can be retrieved from memory and applied to the survey. The facility may be identified from its services or registered functions including, procedures performed, types of physicians, location, insurance accepted, etc. The functions can then be applied as a filter to the survey questions offered along with user preferences and other subjective criteria to arrive at a customized survey.

The physician(s) 414 may also be identified as being part of the facility and/or the survey that follows a patient visit. The treatment plan 416 and overall satisfaction 418 may be indicators which are received from the survey and which are applied to survey questions, results and future records. The results of the survey may be stored in memory 420 for proactive improvement functions described in detail below.

Figure 4B:
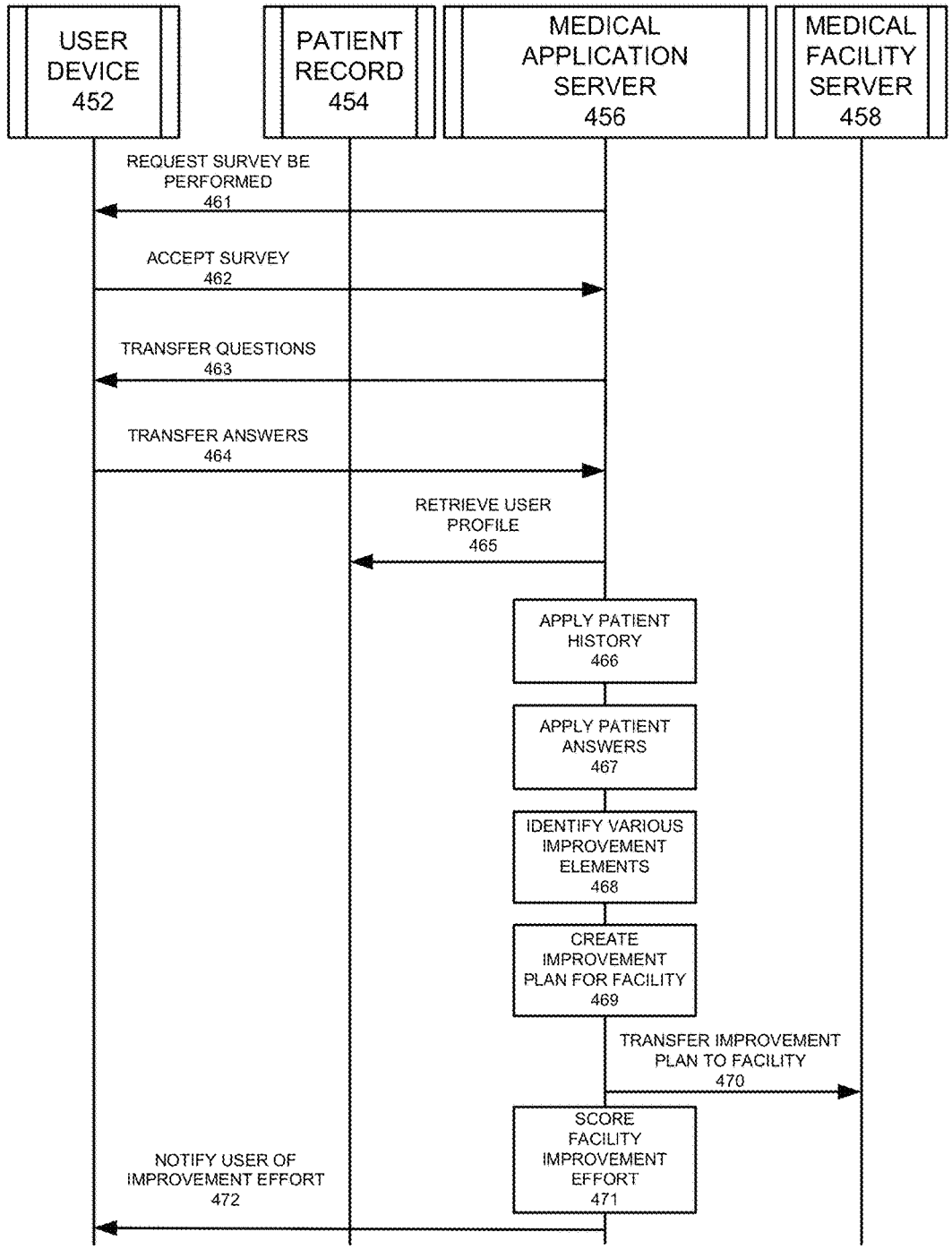
FIG. 4B illustrates a system communication diagram of an example communication process for optimizing medical treatment facilities according to example embodiments.

FIG. 4B illustrates a system communication diagram of the various messaging and communication among the various components of the medical survey portion of the application. Referring to FIG. 4B, the user device 452 may receive a request for a survey to be performed 461 from the medical application server 456. The survey may be transmitted automatically as the patient has completed his or her appointment or has received service from a particular medical facility. The patient may use his or her user device 452 to accept the survey 462 prior to receiving questions or survey prompts from the application server 456.

The questions 463 may then be transferred and answered 464 accordingly. The user profile 465 may be retrieved to customize the questions and to update the line of questioning so the user is profiled as accurately as possible. Next, a patient history may be applied 466 to select questions from a question databank that are based on the types of procedures performed on that particular user, the types of conditions experienced by that user, the types of concerns noted by the user's preferences, etc. The patient answers may then be received, parsed and processed 467 to identify types of concerns including negative statements, positive statements, emergency statements, suggestive comments, wasteful comments, etc.

The parsed patient feedback can then be applied to a set of categories for process improvement, such as facility appearance, facility presentation, staff behavior, physician behavior, quality of treatment, quality of post-office treatment (i.e., follow-up), outcome of care received, etc. That information can be matched to one or more improvement areas and then the content within that predefined improvement topic area can be retrieved and shared with a physician, facility, etc. For example, if the survey indicated that the patient experienced a long wait time to be brought back and seen by the physician, the automatically received feedback may be applied to a known set of improvement standards, such as "Please try to move the patient from the waiting room to an empty station or holding room, it tends to reduce stress on the patient and make them feel more timely during the office visit". Another example would be a message being sent to the facility, such as "Please consider purchasing a brain game station (www.braingamestationpurchasenow.com), the growing trend includes placing the kiosk in the lobby and offering patients an opportunity to play brain games that can then be shared with the physician to prove the patient is coherent and is not senile or experiencing memory loss—this also doubles-up as a way to pass time without experiencing patient dissatisfaction!"

The improvement elements 468 may be identified as a series of suggestions, requests, service orders, or other measures which can assist the facility owners and overseers with decision making necessary to correct ongoing problems, receive maximum insurance payments and perform optimally. An improvement plan 469 may be created based on the stored suggestions and other data and sent to the facility for review 470. The facility may have an ongoing score that is decremented when the poor responses are received that identify that particular facility. Also, a threshold number of responses may be required as a hysteresis measure that can reduce a facility score only once the threshold has been satisfied (i.e., 3 or more negative feedback responses from at 3 or more patients). Also, once the facility has accepted a process improvement suggestion or strategy, the facility score may automatically increase based on the assumption that the facility will improve or fix the alleged problem in the near future. An improvement score may be noted 471 and a notification may be sent to the user to inform the user of the possibility of immediate improvement.

Figure 4C:
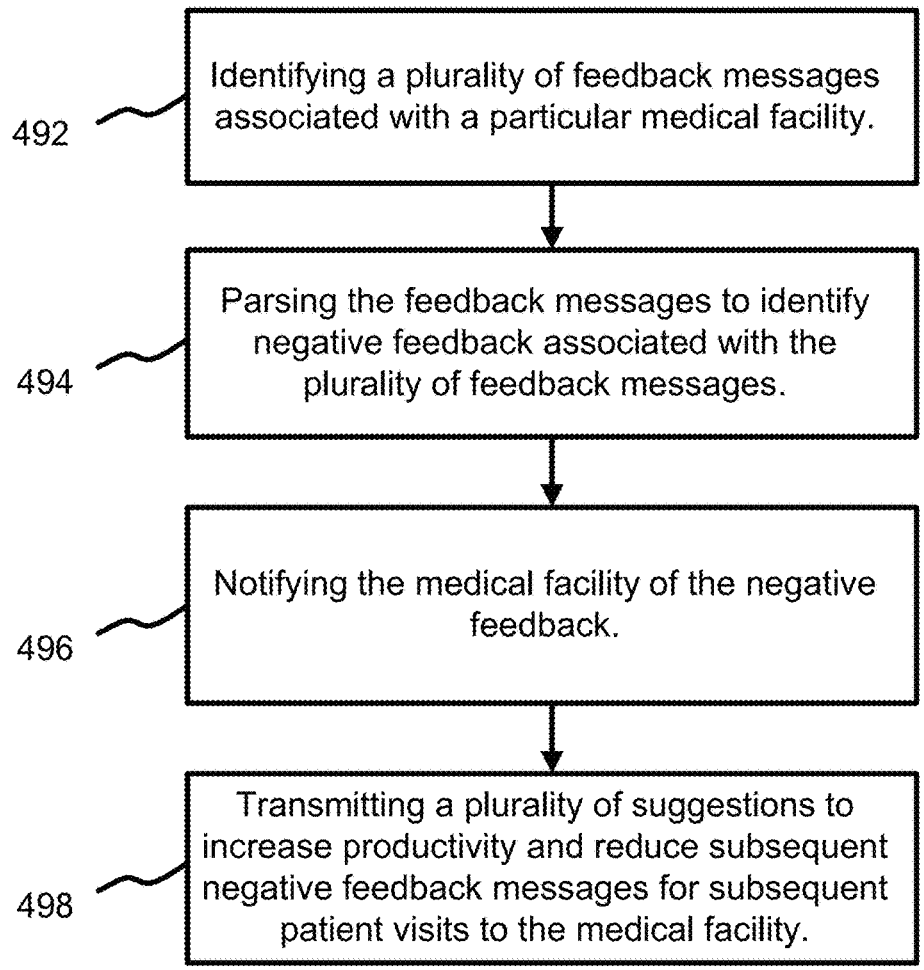
FIG. 4C illustrates an example flow diagram of an example method of operation according to example embodiments.

According to one example method of operation 490 of FIG. 4C, a method may provide identifying a plurality of feedback messages associated with a particular medical facility, at operation 492, and parsing the feedback messages to identify negative feedback associated with the plurality of feedback messages at operation 494. The method may also include notifying the medical facility of the negative feedback at operation 496, and transmitting a number of suggestions to increase productivity and reduce subsequent negative feedback messages for subsequent patient visits to the medical facility at operation 498.

During the process of identifying the negative feedback, the procedure may also include identifying a target problem area based on the parsed feedback messages among various different areas for improvement. Those known areas can be stored in memory and the set of improvement suggestions can be retrieved from a database that correlates to the target problem area. The improvement suggestions can be retrieved and sent to the medical facility which then provides a confirmation that at least one of the improvement suggestions will be enacted. The facility may have its service score increased responsive to receiving the confirmation, and the medical facility service score can then be updated.

In other examples, a notification can be transmitted to at least one user associated with a user profile that submitted negative feedback about the medical facility via a survey, the notification indicates the medical facility's compliance with the improvement suggestion and may also include a request to schedule another appointment as a follow-up measure. If the user wants a new appointment, the appointment confirmation may be received responsive to the transmitted notification. The user's medical record can then be updated to indicate the appointment and the negative feedback about the medical facility. Also, an appointment notification can be sent to the medical facility that includes the appointment time and the negative feedback. The negative feedback may be any of wait time, prescription compliance, physician conduct, staff conduct, medical treatment, and follow-up compliance. Among the feedback, a target problem can be identified based on the parsed feedback messages. The target problem may be selected among a number of target problem areas including patient satisfaction, physician compliance/non-compliance, staff procedures and follow-up procedures.

According to another example embodiment, the medical facility may have an advanced scheduling algorithm and dynamic re-scheduling function. In most facilities, the schedule is quit full and any missed appointments will cost the facility large sums of revenue lost. In this example, the facility will implement a medical assistant application scheduling function that relies on patient history, patient profiles and other useful information to optimize a patient/physician schedule.

A typical scenario includes a patient having a scheduled appointment with a physician and not going through with the appointment and not calling to reschedule to a later time. In such a case, the medical assistant application can log the user and update his or her profile to reflect this type of event. The medical facility will want to reduce the number of 'no-show' appointments and one way to implement this strategy is to identify users who are likely to commit this offense. Those patients are not barred from visiting the office, however, knowing ahead of time which ones are likely to forget or cannot find the time to be present at the scheduled time may provide an advanced algorithm for optimizing present day schedules for maximum efficiency.

Patient feedback may be collected from known data sources, such as feedback forms submitted online, feedback forums or websites, etc. The data may be collected periodically and analyzed by a processing engine commissioned by the medical facility seeking to improve its appearance and overall service. The feedback may be collected and categorized, summarized and organized to present to a live committee or to certain recipients who may have filters setup for certain criteria, such as quality, money, health problems, etc. If a customer has a suggestion that is incorporated into the improvement effort, that customer may be identified by his or her identification information and linked to a bonus award since their contributions were accepted and used to change certain procedures at the facility.

Figure 5A:
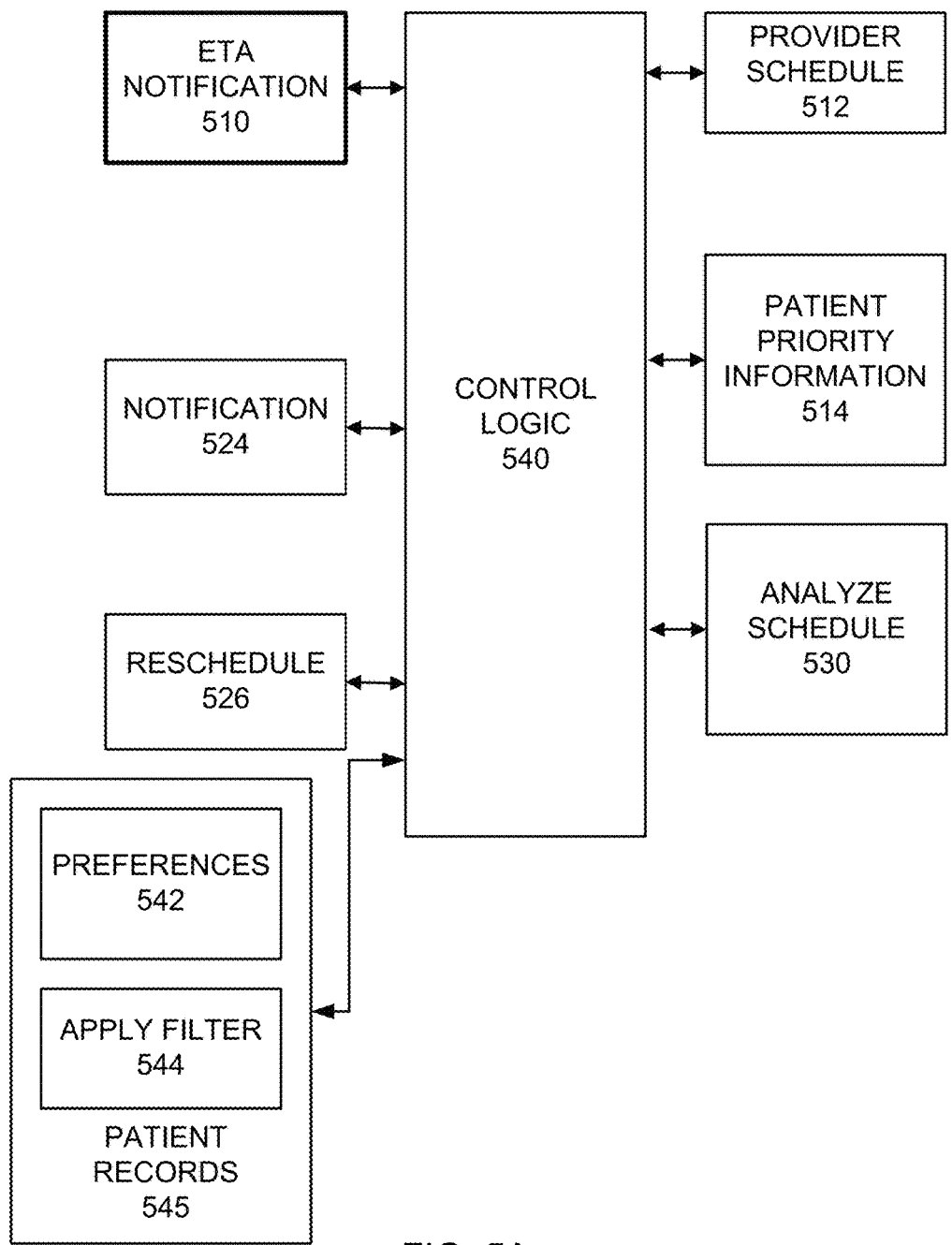
FIG. 5A illustrates an example logic diagram of a patient health care application for identifying patient treatment facility options according to example embodiments of the present application.

FIG. 5A illustrates an example logic diagram of a user or patient scheduling and management operation according to example embodiments. Referring to FIG. 5A, the diagram 500 includes a control logic processor 540 which receives input, such as an estimated time of arrival 510 or schedule reservation parameter and identifies a provider schedule 512 so an appropriate time can be identified and scheduled as a next day appointment. Initially, the patient may be identified via his or her patient record and the record may indicate the patient's priority 514 based on factors, such as severity of health condition=priority high, age (under 6 months, over 75)=priority high, previous appointment history, etc. The patients who have been on time for all previous appointments may be ranked significantly higher than those who are later or don't show-up at all. The present schedule can then be analyzed 530 and the patient priority can be applied to select a time slot for the patient's next appointment.

Notifications 524 may be transmitted to the user devices to indicate when the appointment is scheduled with an option to reschedule. The rescheduling 526 may take place based on the user feedback or via other rescheduling criteria, such as a lack of response from the user device, distrust in the patient based on history data, etc. User preferences 542 may be applied as a filter 544 to setup an appointment via a filter 544. For example, the preferences for distance may be setup to a location at a multi-location facility that is closest to the patient's house. The patient records 545 may store all the necessary data to populate the appointment schedule based on known patient parameters.

Figure 5B:
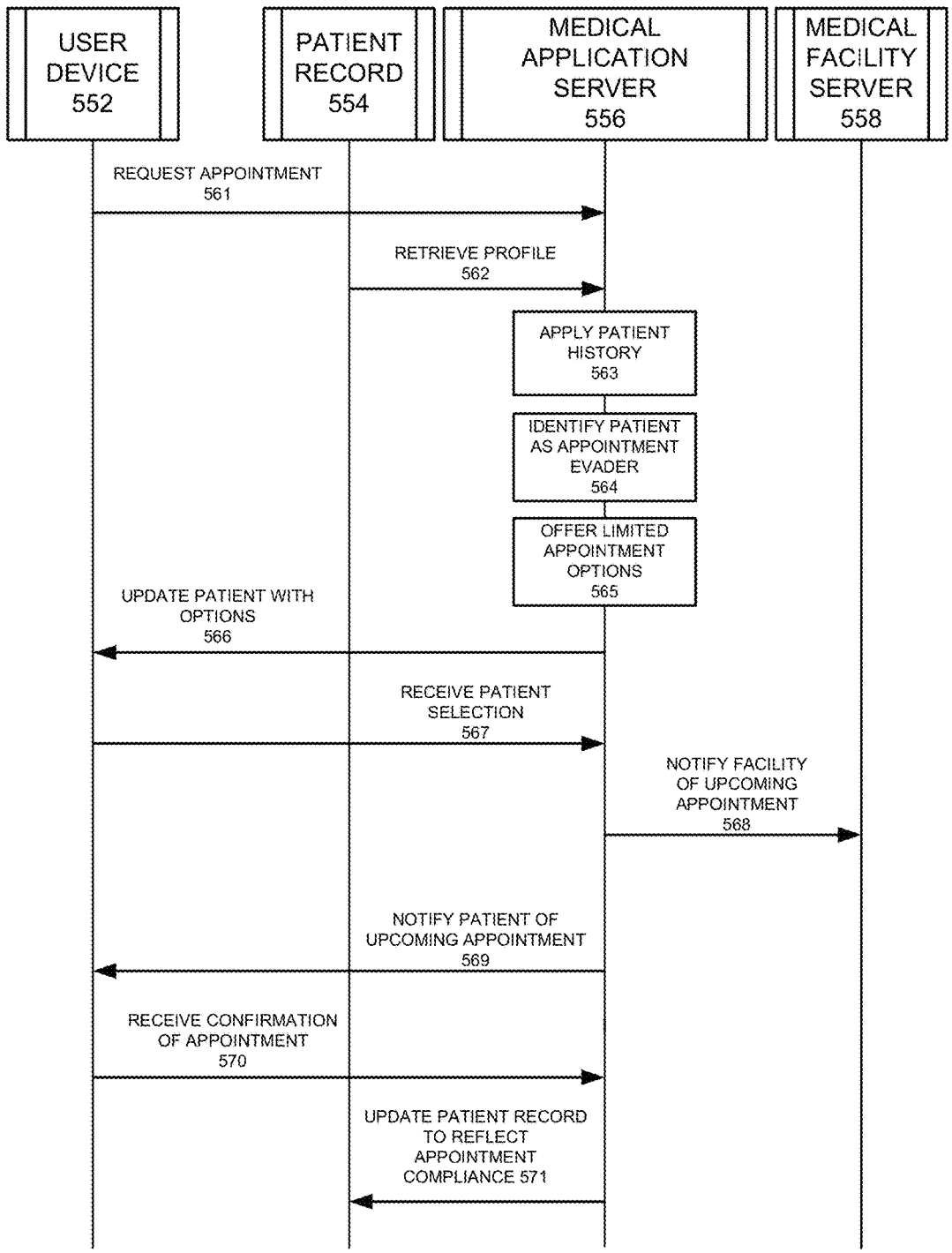
FIG. 5B illustrates a system communication diagram of an example communication process for identifying patient treatment facility options according to example embodiments.

FIG. 5B illustrates an example communication signaling diagram 550 according to example embodiments. Referring to FIG. 5B, the user device 552 may request an appointment 561 to see a physician or have a procedure performed. The medical application server 556 may receive the request, retrieve the patient profile 562 from the patient record 555 and apply the patient history to the appointment scheduling process 563. The patient can be identified as either new or previously known and as a conforming patient who accepts and maintains the appointments provided or alternatively the patient can be identified as an appointment evader 564. Those patients who are more likely to miss a scheduled appointment are then placed in a scheduling algorithm that limits the amount of appointment opportunities 565 by only offering half or limited time slots that are not as likely to result in loss of revenue for the facility if the patient does not show-up to the appointment. These limited time slots are scheduled at off-times and generally between actual time slots as times when the medical facility is least likely to have nominal resources available and is otherwise engaged in actual time slot or preferred time slot appointments. The options may be presented to the user device 566 and a selection may be received 567 assuming the appointment was not already setup for the patient. The scheduled appointment can then be transmitted to the medical facility server 558 via a notification 568. Subsequently, a reminder may be transmitted to the user device 552 to identify the upcoming appointment. If the user profile is that of an appointment evader or a less prioritized patient, then the notification 569 may require a response 570 or else the appointment may be cancelled automatically via the application. The patient's record may be updated 571 to reflect the appointment compliance by increasing the patient's compliance score, recording the event of the appointment being satisfied, upgrading the patient's present priority (e.g., low, medium, high, excellent).

When identifying a patient's likelihood to show-up in time and fulfill their appointment obligation, some possible patient and appointment attributes to consider when identifying the outcome may include the patient's medical record number, appointment date, time, disease, doctor's name, appointment reason, appointment booking source, pain level, check-in time, check-out time, weather condition, transportation condition, additional significant conditions, such as relevant breaking news (school shooting, etc.), occupation.

In operation, when a patient missed their check-in time or window (i.e., 15 minutes after appointment time). Upon detecting this condition, the system may also capture additional relevant data items, such as weather, transportation condition, news, etc. In one example, an annual check-up for a patient may be scheduled at 8:30 AM. This appointment may have a higher probability to be missed since the "pain level" is 0 or non-existent and it is first thing in the morning. Certain solutions may include when the appointment was made, a confirmation may be sent along with options to include travel time to the doctor's office. Two results from this interaction may include permitting or triggering an option for the patient to "import" the appointment into their calendar, such as MICROSOFT OUTLOOK, GOOGLE CALENDAR, etc., and add additional travel time into this schedule.

During the appoint setup interaction, the patient can be asked where are they going to be traveling. For example: "Will you be driving from work to this appointment?", which yields two data points: transportation=driving, coming from=work. One day before the appointment date, another interaction is initiate and a message may be delivered to the patient. The goal of this interaction is to remind the patient of the appointment, provide additional instructions about the appointment, for example bring your current medications, weather information, such as alert the patient of potential weather condition during the appointment time, travel information, such as alert patient of any road construction or closings that may cause delay, and provide the opportunity to reschedule at any time. On the day of the appointment, another interaction is sent an hour before the appointment time, for example "8:30 AM appt. with Dr. Johnson is on time". If appointment is running behind, a notification may be sent along with other time options for the same day. For example: "8:30 AM appt. Dr. Johnson is running behind. Your appointment is now at 8:50 AM. Other available times are 4:00 PM and 4:30 PM . . . ." Also, other relevant data: weather, traffic, etc. may be included as an update. The patient should be able to reschedule the appointment if needed.

Patients could be motivated to start showing-up on time by creating a "points" scheme so the more times they show up on time, the more points they gain. They can use/cash in those points to create "high priority appointments" where they could conceivably bump someone out of another appointment slot or get the appointment slot given to them in the event that both patients wanted the same day/time and booked at exactly the same time. Similarly, patients might have their names or account status be placed in a point demerit or negative point position each time they miss an appointment. The more appointments the patient is late for, the more points they keep losing, the lower on the priority list they become when they go to make future medical appointments.

Figure 5C:
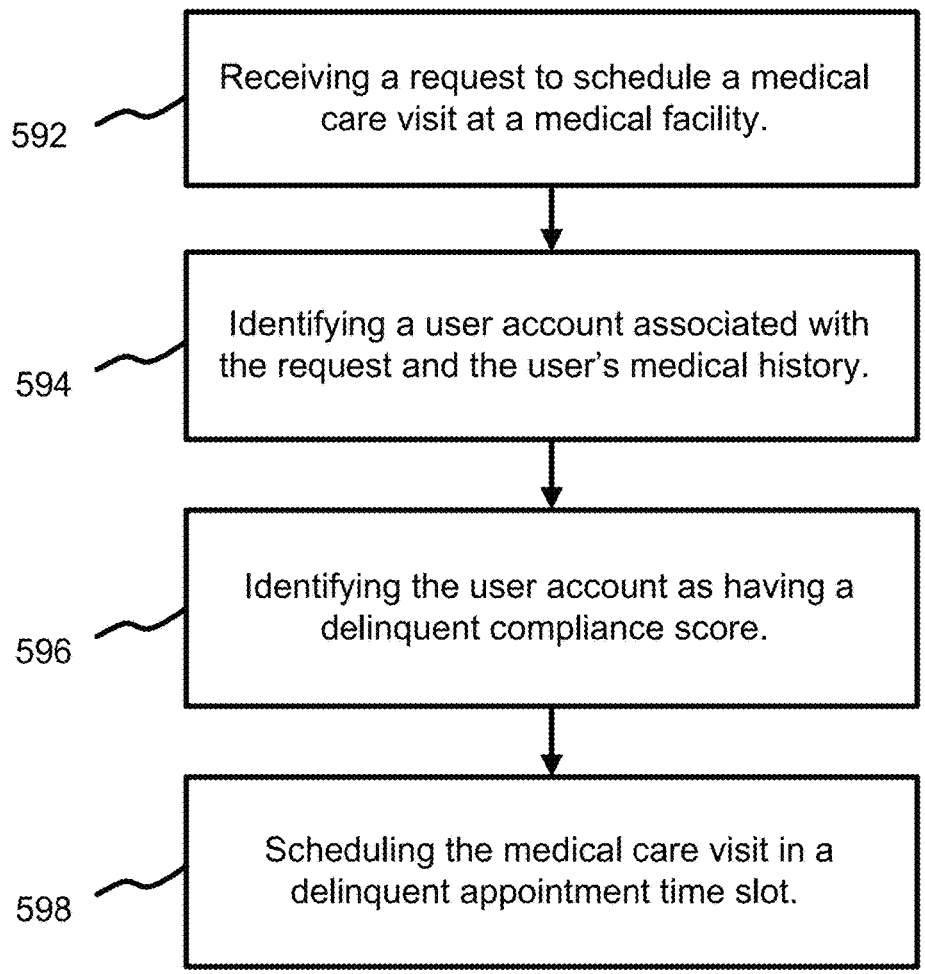
FIG. 5C illustrates an example flow diagram of an example method of operation according to example embodiments.

FIG. 5C illustrates an example method of operation according to example embodiments, referring to FIG. 5C, the method may include receiving a request to schedule a medical care visit at a medical facility, at operation 592. The request is processed and the user profile may be retrieved to identify a user account associated with the request and the user's medical history to identify previous appointments and compliance at operation 594. The method also provides identifying the user account as having a delinquent compliance score if the patient has missed an appointment scheduled previously at operation 596. The method also includes scheduling the medical care visit in a delinquent appointment time slot at operation 598 since the patient has a lower priority due to previous patient history.

In another example, the scheduling of the medical care visit in the delinquent appointment time slot may include identifying a partial time slot between two established regular time slots. This time slot may be lesser in time (15 minutes vs. 30 minutes or 30 minutes vs. 1 hour). The lesser time slot can be assigned and transmitted as an option to the user device to schedule an appointment in that partial time slot. The method may also include creating the appointment based on the user device selection received, receiving confirmation the appointment occurred, and updating the user's medical record to indicate the appointment occurred and to increase the user's compliance score. The compliance score may be numerical value that is incremented or decremented to identify compliant or non-compliant actions. The compliance score may also be a priority level, such as excellent, high, medium, low and lowest. The lower priority receives fewer options for appointment times.

In another example, the method may include receiving a confirmation message that the user account has achieved a nominal rating and in such a case, the user's compliance score may be increased above a predetermined threshold. Next, an update message can be transmitted to the user device to inform of the recent compliance score increase and to offer a scheduling opportunity that was not previously offered. The patient may then accept this recognition and transmit a new scheduling request from their user device. The application may then schedule a new appointment in a regular time slot responsive to receiving the new scheduling request. The user preferences may be applied to a scheduling algorithm, and the new appointment may be automatically setup and scheduled based on the user preference, and the new appointment time may be transmitted to the user device for confirmation. An exception may include identifying a severe medical condition from user's medical history or other extenuating circumstance, overriding the delinquent compliance score, and scheduling the medical care visit in a normal appointment time slot since the user cannot be limited due to the severity of the circumstances.

According to another example embodiment, the scheduling of a patient appointment may be setup and modified according to an arbitrage algorithm that seeks to setup as many appointments as possible while sorting through the present appointment schedule to make changes or offer incentives to those who are willing to accept modifications to their present schedule. For example, a full schedule on any particular day may change when an urgent matter arises and someone needs to be seen immediately. The appointments of that day which belong to patients with flexibility may receive an invitation to change their appointment in return for a $10 reduction in copay if they accept their appointment change to the next day. This process is similar to the airline industry's overbooking strategy of offering rewards to those willing to accept them in return for relinquishing a seat on a present flight.

Figure 6A:
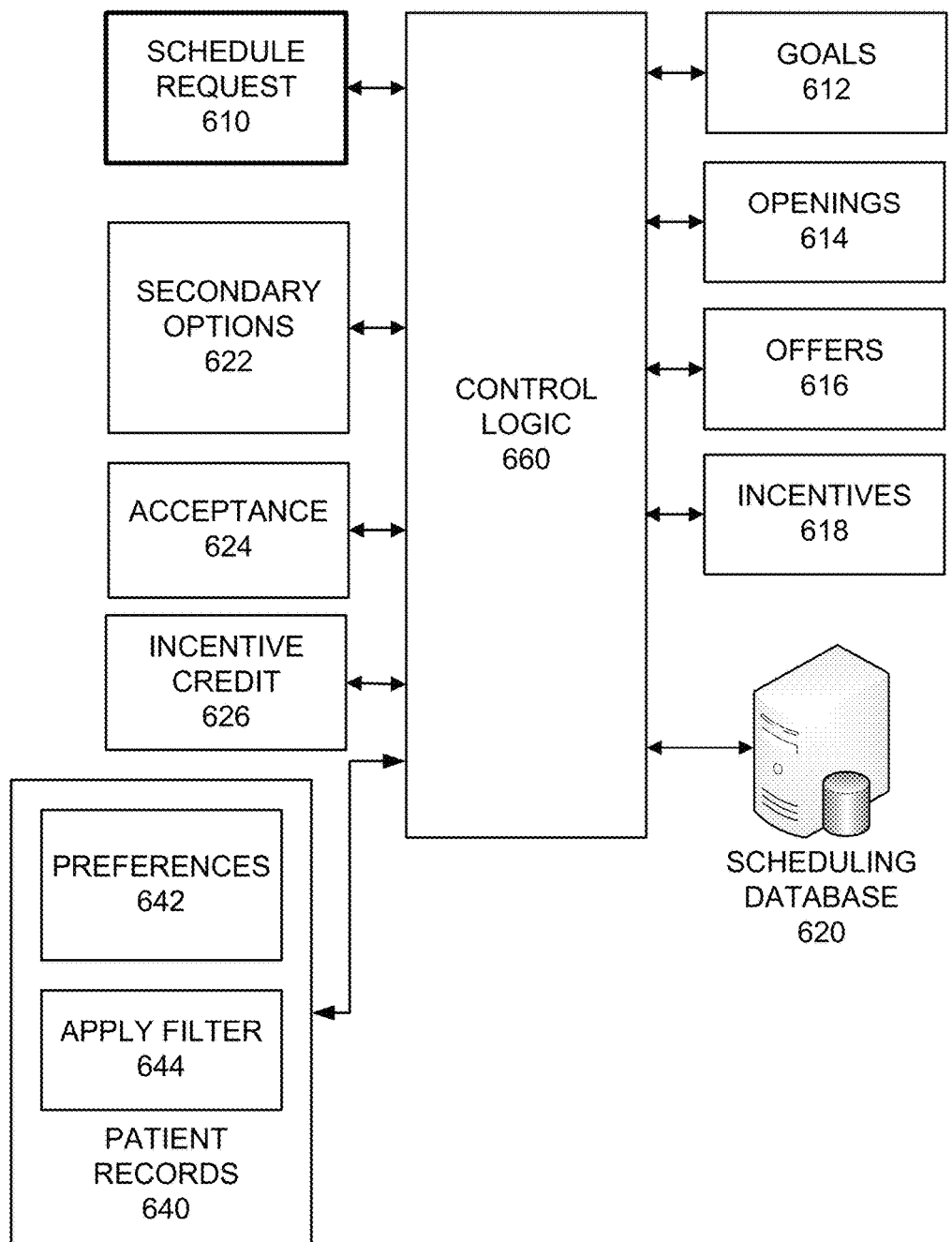
FIG. 6A illustrates an example logic diagram of a patient health care application for identifying and optimizing physician scheduling according to example embodiments of the present application.

FIG. 6A illustrates an example logic diagram of a scheduling arbitrage algorithm according to example embodiments. Referring to FIG. 6A, the logic diagram 600 includes a control logic processor 660 which receives input parameters, such as a schedule request 610 from a user device. The scheduling algorithm may identify the facility goals 612, such as schedule capacity, day of the week, etc., the present openings 614, etc. and may prepare a first and second scheduling result and transmit the options to the user device which receives the various options 622 and provides an acceptance 624 or rejection. The schedule may dynamically change over the course of time by trying to overbook to ensure compliance and maximum capacity due to no-shows or emergency appointments which must be accommodated on-the-fly. As the schedule requires adjustment, the offers are generated 616 based on internal incentives (e.g., maximizing capacity), such as no-copay, half-copay, etc. and are paired with an alternative scheduling scenario (second or third choice) to the user device.

The scheduling database 620 stores the results and updates the schedule according to the algorithm. Each user may have his or her patient records 640 referenced to provide user preferences 642 via a corresponding data filter 644. For example, the user preferences may always dictate no Friday appointments, therefore, when a modification to a scheduled appointment must be made for a particular user profile, then the secondary scheduling effort may offer alternatives that are not on Friday so as to correspond with the user preferences 642. As a user accepts the rescheduling options, the user receives a scheduling credit 626 which may be monetary, priority-based or provide other types of incentives to the user profile when scheduling or visiting the facility.

Figure 6B:
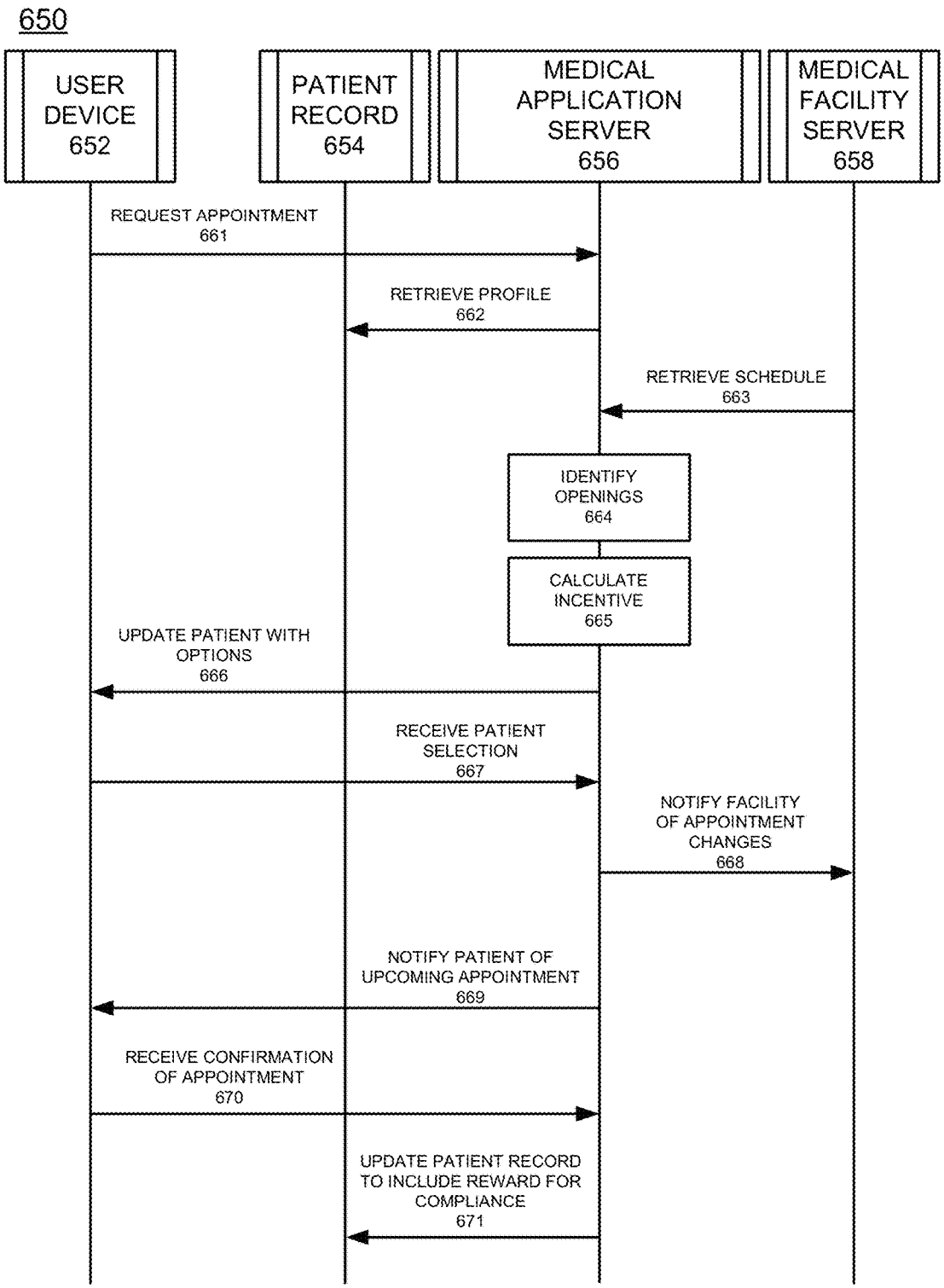
FIG. 6B illustrates a system communication diagram of an example communication process for identifying and optimizing physician scheduling according to example embodiments.

FIG. 6B illustrates an example of a system signaling diagram of a medical facility scheduling algorithm according to example embodiments. Referring to FIG. 6B, the diagram 650 includes a user device 652 transmitting a request for a medical facility appointment 661 to the medical application server 656. The application server 656 may retrieve a patient profile 662 from the patient record 654 and a present schedule from the medical server 658. The algorithm can now identify openings in the schedule 664 and apply the patient profile to the schedule creation (e.g., preferences, special needs, etc.). Next, any available incentives 665 can be calculated and used to generate schedule modifications to optimize the availability of the facility while trying to satisfy the user's preferences.

As options for the patient become available, the patient may be updated with options 666 for scheduling, such as option #1—no incentive, option #2—incentive option $10.00 credit, option #3—no incentive. The patient may select one or more options in a particular order to provide options to the medical facility. The application may receive the selection 667 and the facility may update the schedule accordingly 668. The patient is notified of the upcoming appointment 669 via a SMS message or other message transmitted to the user device. The user device may receive confirmation of the appointment and transmit a confirmation that the appointment is still active 670. The patient record 654 may be updated and the reward for compliance can be credited 671 assuming the user has earned a reward for accepting a modified appointment or an incentivized appointment.

Figure 6C:
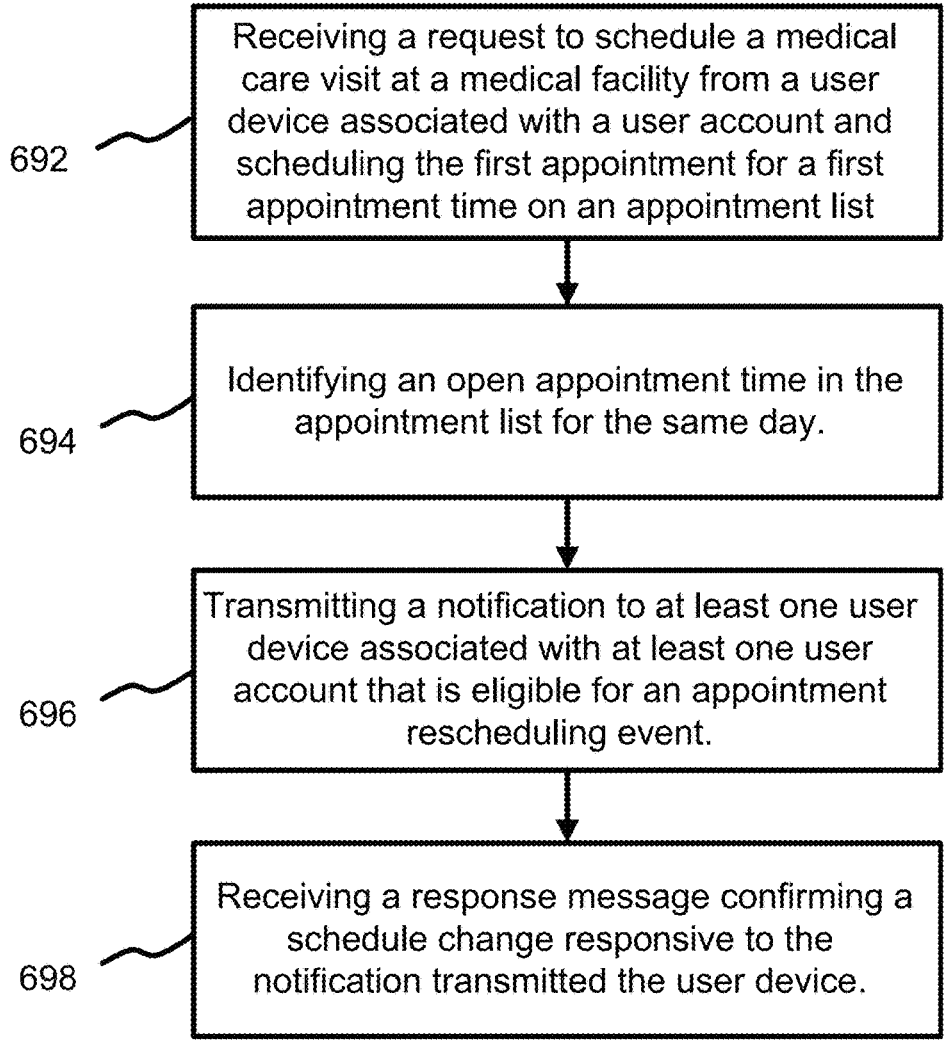
FIG. 6C illustrates an example flow diagram of an example method of operation according to example embodiments.

FIG. 6C illustrates an example of a method of operation according to example embodiments. Referring to FIG. 6C, method may include receiving a request to schedule a medical care visit at a medical facility from a user device associated with a user account and scheduling the first appointment for a first appointment time on an appointment list at operation 692. The scheduling may attempt to satisfy the user's request, however, multiple times may be presented based on availability. The method may also include identifying an open appointment time in the appointment list for the same day as the request at operation 694. The method may also include transmitting a notification to the user device associated with the user account that is eligible for an appointment rescheduling event at operation 696. In this example, the original appointment is going to be rescheduled and certain options will be presented to the user device for selection. The method also includes receiving a response message confirming a schedule change responsive to the notification transmitted the user device at operation 698.

During the rescheduling procedure, an incentive for the appointment rescheduling event may be identified due to a need to move the appointments currently scheduled to accommodate others. In this example, the first appointment may be rescheduled to the open appointment time different from the first appointment time, and confirmation from the user device may be received for the rescheduled appointment at the open appointment time. In this example, the user account may be credited with accepting the schedule change and the user account may be updated to reflect the credit received for subsequent medical visits. The credit received includes a prioritized time schedule and/or a financial reward. The user account may be identified as being credited with the incentive, and one or more user preferences can also be retrieved and associated with the scheduling. Assuming the user has received credit, has a special need or a special circumstance type of account (e.g., chronic condition, infant, elderly, etc.) then the prioritized scheduling algorithm may offer the user account priority for scheduling the appointment(s).

In another example, the algorithm may identify an open appointment time slot within a predefined number of days from the present day, generate incentives for appointments accepted during the available open appointment time slots, and transmit the open appointment time slots to the user device for selection. As a result, one or more selections may be received from the user device, and the user account may be credited with accepting the open appointment time slot.

Another example embodiment may provide a patient appointment setup configuration that identifies insurance compliance, fraud protection measures and other processing functions for medical facility optimization. For example, a user or patient may attempt to setup an appointment for a particular type of physician or procedure. However, the medical insurance may be limited in its policies and rules which govern those types of procedures sought by the patient. In such a case, it is preferred to have the analyzing and screening performed ahead of the appointment to avoid a non-reimbursable scenario.

A patient or customer could gain "points" in return for accepting changes. The points can be saved up by the customer and can be used by customers to obtain a higher priority or to move appointment requests to the front of the queue for a future medical appointment. For example, if a patient is offered and agrees to a threshold number of (i.e., '3') appointment changes the patient account may gain 3 points which can then be used to obtain first priority appointment preferences for future medical appointment requests. The desire to have preferred status could result in increased loyalty to the medical facility and increase patient retention thus driving more business and increased satisfaction for both the facility and the patient.

Accumulated points may also be redeemed by customers to receive the surgery or doctor appointment time of their choice. For example, a patient might have a particular preference one day for a 10 am appointment but the doctor only has a 9 am time slot available. In this case, the patient who has saved up enough "points" can actually trump someone else who currently has the 10 am spot booked. The loyal or higher priority patient receives the 10 am spot and the person who had it before, simply receives a notice that the doctor office needs to change the day/time of their appointment (e.g. from 10 am to 9 am). Instead of points, the patient may instead in another example receive recognition in a social media context, such as the "most considerate patient award" for the month or something similar. The facility may even make a $10 donation to the charity of the patient's choice or something similar.

Figure 7A:
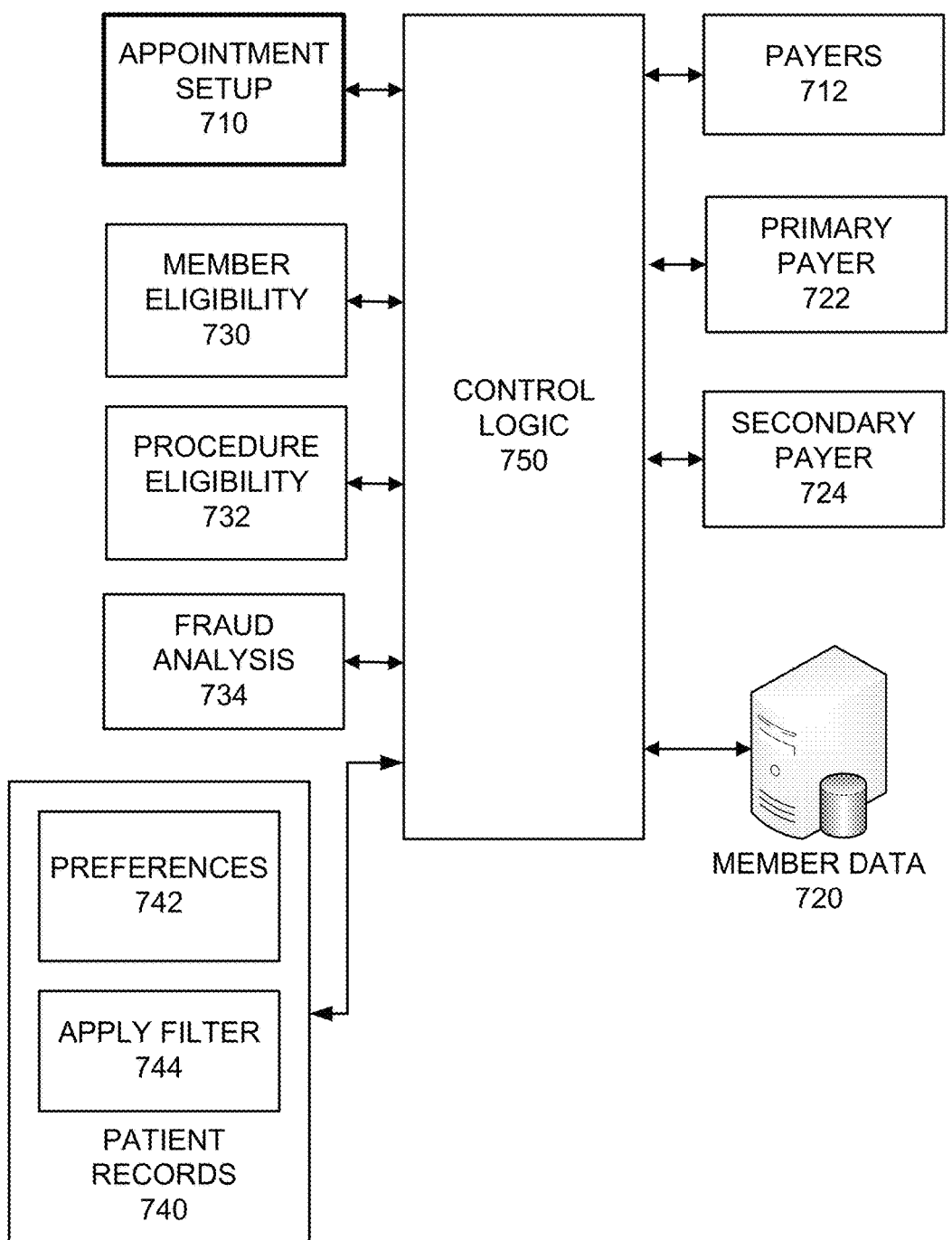
FIG. 7A illustrates an example logic diagram of a patient health care application for identifying and optimizing schedules and payment options according to example embodiments of the present application.

FIG. 7A illustrates an example logic diagram of a scheduling arbitrage algorithm according to example embodiments. Referring to FIG. 7A, the patient may have at least one insurance policy through a job or through a spouse's job. The patient may seek an appointment 710 which the control logic processor 750 may process the request along with present member eligibility 730, specific procedure eligibility 732 and perform a fraud analysis to ensure the patient has not sought that procedure elsewhere thus limiting the medical facilities ability to collect payment on such a procedure if the appointment is created. The medical facility may store the payer information of such services 712 including a primary payer 722 and a secondary payer 724 (supplemental insurance). The member data may be stored and updated 720 when new insurance policies are identified or old ones are no longer active. When scheduling an appointment or providing a service to the patient, the preferences 742 may be applied by a filter 744 that is stored in the patient records information 740.

Figure 7B:
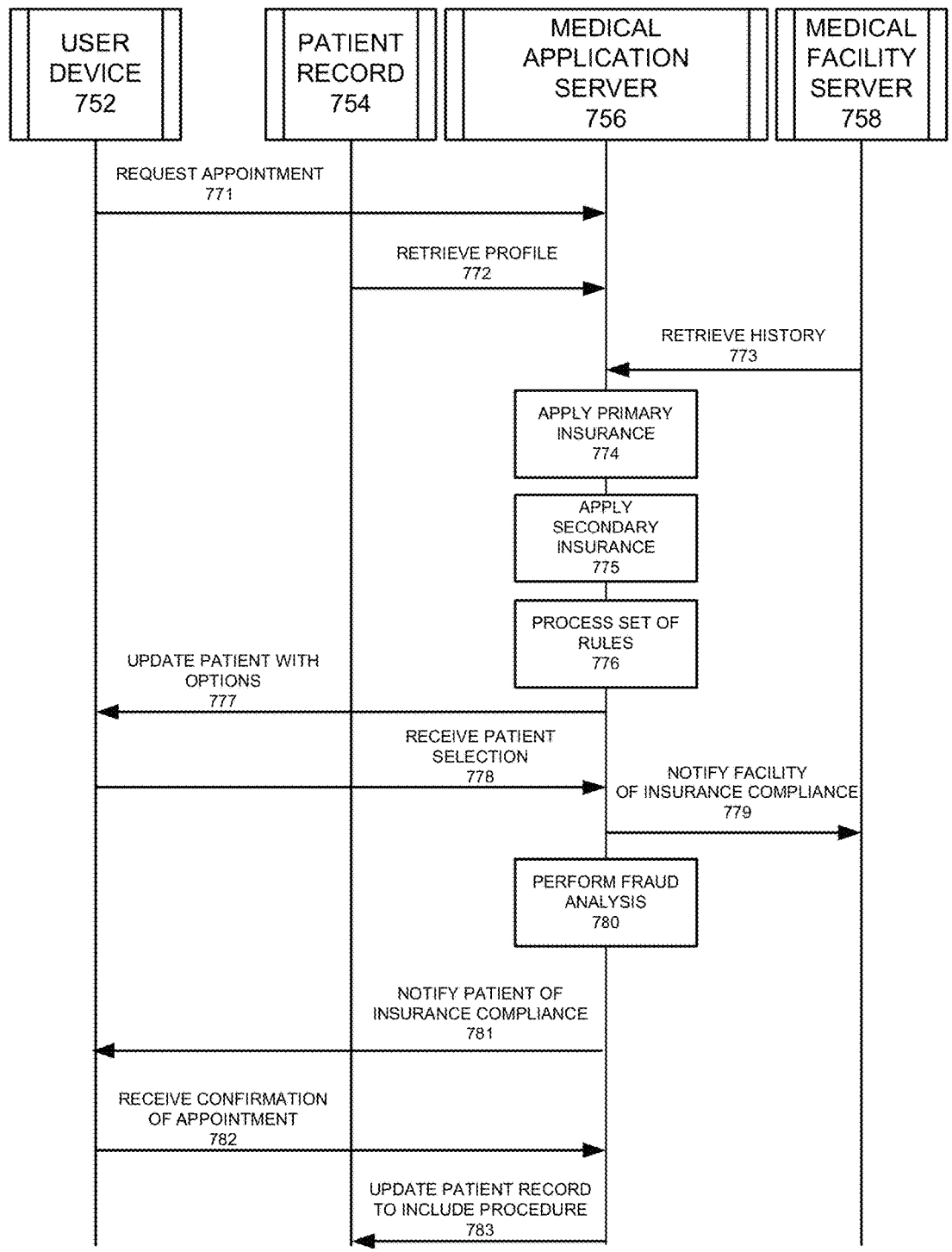
FIG. 7B illustrates a system communication diagram of an example communication process for identifying and optimizing schedules and payment options according to example embodiments.

FIG. 7B illustrates an example of a system signaling diagram of a medical facility scheduling algorithm according to example embodiments. Referring to FIG. 7B, the system diagram 750 includes a user device 752 initiating a request for an appointment (e.g., colonoscopy, dermatologist skin procedure, etc.). The medical application server 756 may retrieve the patient record 754 based on the authenticated user device 752 and extract the patient profile 772 to identify a validation of such a procedure desired. The history information may be retrieved 773 from the medical facility server 758 and applied to a current insurance policy 774 to identify any rules 776 which may apply in either the current policy 774 or the secondary policy 775, if available. The policies will be examined for rule compliance, the history of the patient will be analyzed and the result of the determination may be setup to be shared with the user device 752 of the patient for validation and acceptance based on one or more options 777 and selections 778. The facility 758 can then accept the appointment 779 with certainty that the procedure will be paid by the insurer. A fraud analysis may also be performed 780 to identify if the patient is actually the same as the insured party and whether the patient has had such procedure performed at another location. Finally, the patient may be notified of the compliance 781 and the appointment may be confirmed 782 via the user device 752. The patient record 754 can be updated to reflect the procedure being scheduled 783.

Figure 7C:
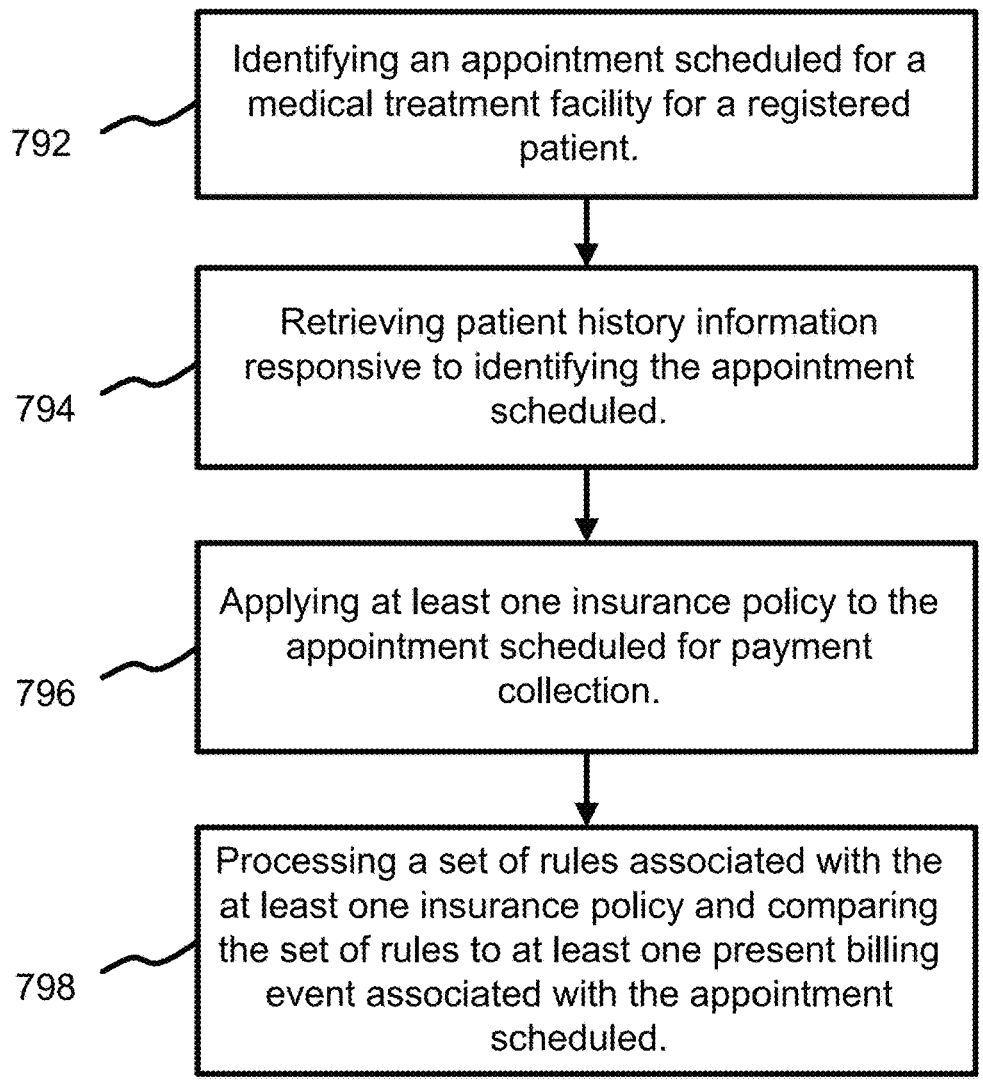
FIG. 7C illustrates an example flow diagram of an example method of operation according to example embodiments.

FIG. 7C illustrates an example of a method of operation according to example embodiments. Referring to FIG. 7C, an example method of operation may include identifying an appointment scheduled for a medical treatment facility for a registered patient, at operation 792, and retrieving patient history information responsive to identifying the appointment scheduled at operation 794. The method may also include applying a first insurance policy to the appointment scheduled for payment collection at operation 796 and processing a set of rules associated with the insurance policy and comparing the set of rules to a present billing event associated with the appointment scheduled, at operation 798.

The method may also include identifying the set of rules prohibit reimbursement for the present billing event and identifying a secondary insurance policy associated with the registered patient. This provides a way to consider an alternative to the present insurance policy. Then, the billing event may be applied to the secondary insurance policy responsive to identifying the set of rules prohibiting reimbursement from the first policy. Or, there may be no active policy that provides the user with any recourse, so an automated message may be transmitted to the user identifying that the procedure may not be covered and will cost X dollars to provide. The user may receive a non-insured discount and may accept that option via a message from the user device.

In another example, a fraud analysis may be performed to determine whether the insurance policy has already been applied to a previous procedure that is comparable to a present procedure identified from the present billing event. The process may also confirm the patient has not experienced a previous procedure that is comparable to the present procedure based on a query of patient records or via other data retrieval operations. Once the fraud analysis is confirmed, a payment request may be generated and transmitted to the insurance policy provider.

In another example, a notification may be received that the primary insurance account holder and/or the secondary insurance account holder has changed job status. This normally implies that the policy is no longer active. The application may generated a notification to notify the primary insurance account holder and/or the secondary insurance account holder of the change. Next, a confirmation of a new insurance policy may be received and used to update the user profile. As a result, a new insurance form may be generated via a web application, and transmitted to a user computing device of the user so the policy can be corrected in real time. A new insurance provider may be identified along with a new policy number from data associated with the form. Such data may be used to update the user profile to include the new insurance provider and the new policy number.

According to another example embodiment, the user device may provide a source of continued user diagnostic monitoring and management. For example, the user device may have a wired or wireless communication interface that corresponds to a blood pressure monitor attached to a user, a heart rate monitor attached to the user and/or a blood sugar sensor operated by the user. The user device may notify the user periodically about the need to collect such data and store the data in a tabular list for the present time, day, week, etc. The data may be uploaded to a remote application server for processing and comparison operations that identify whether the user is eligible for a physician visit or requires emergency medical treatment. Also, the patient may be fine and may be in need of reminders that the health status appears to be stable pending further review.

Figure 8A:
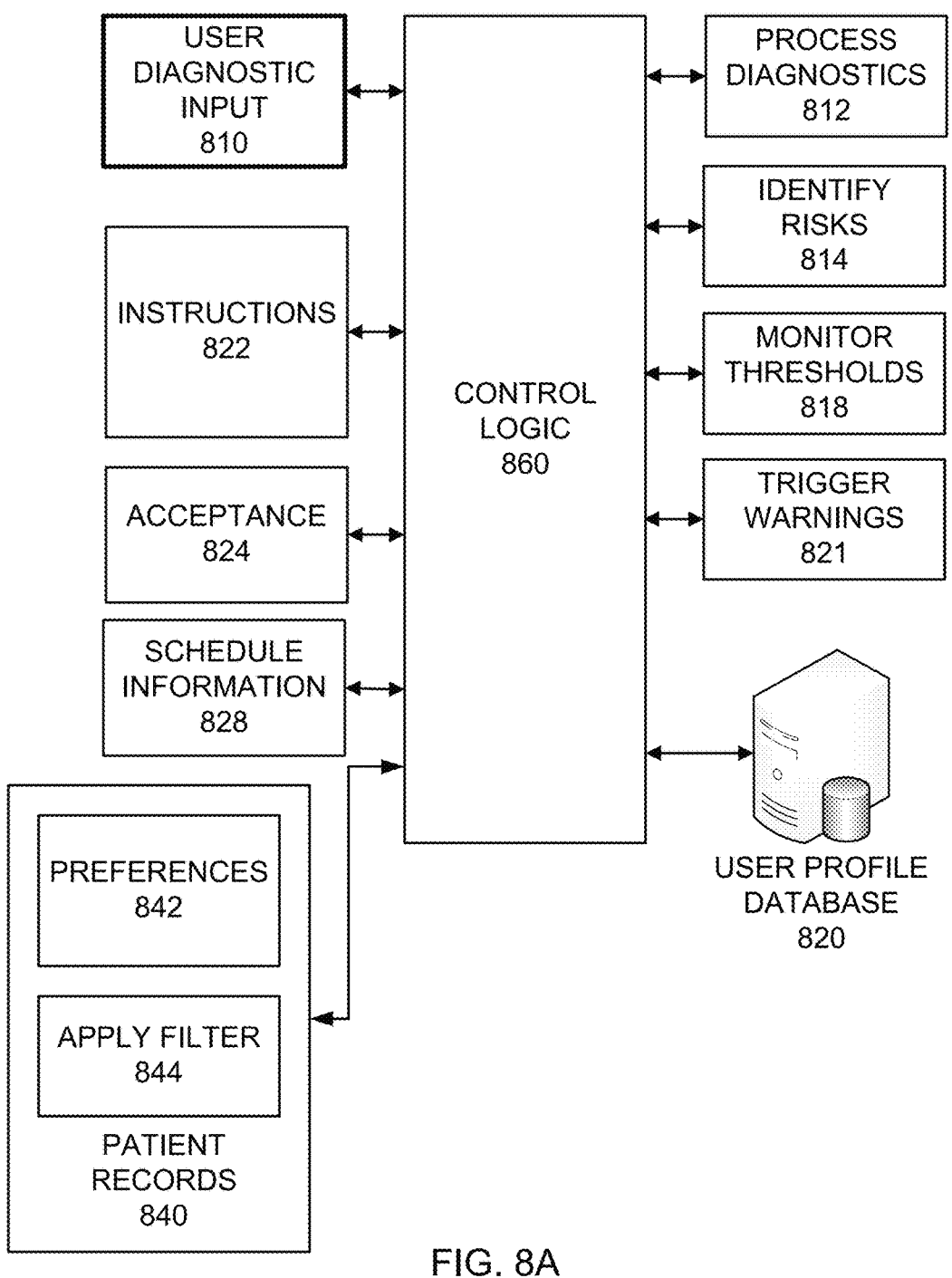
FIG. 8A illustrates an example logic diagram of a health insurance claim processing application according to example embodiments of the present application.

FIG. 8A illustrates an example logic diagram of a patient management algorithm according to example embodiments. Referring to FIG. 8A, the logic diagram 800 includes user input via the electronic body worn sensors which interface with a data input interface of a user computing device. The user diagnostics may be received as data input 810 and processed via the control logic processor 860. The data may be processed as a set of different diagnostics 812 and certain risks can be identified 814 depending on the patient's present status and the baseline comparison. For example, the monitor thresholds 818 may be established as limits on heart rate, blood sugar, blood pressure, etc. which if exceeded or in some case if they user data is lower than the threshold, then an alarm may be triggered that notifies the patient's physician, medical treatment facility, 911, etc. The thresholds may be the basis for initiating trigger warnings 821 which notify the appropriate interested parties.

In one example, the patient may qualify for a patient visit with a physician or other medical treatment specialist based on the received diagnostic data. The user device may receive an invitation to accept an appointment, a phone call, or even an email or text message. In such a case, the user may accept the appointment 824 and receive a schedule for the appointment or a course of action 828. Certain instructions 822 may be received by the user to alleviate the elevated condition identified from the diagnostic data. The information may be stored in the user profile database 820. The patient records 840 may include preferences 842 and a corresponding filter to provide more appropriate care to the patient based on his or her preferences.

Figure 8B:
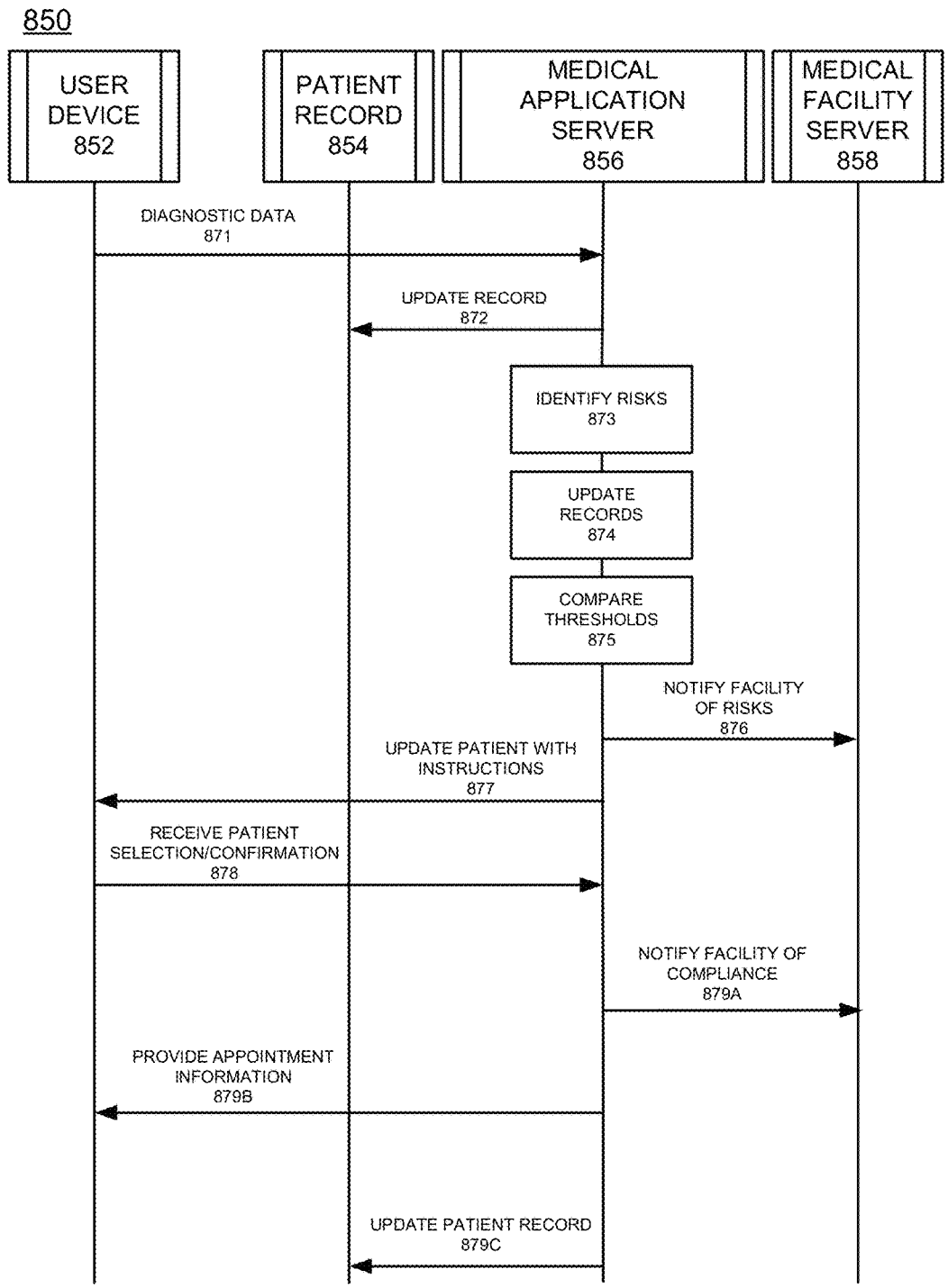
FIG. 8B illustrates a system communication diagram of a health insurance claim processing application according to example embodiments.

FIG. 8B illustrates an example of a system signaling diagram of a medical facility scheduling algorithm according to example embodiments. Referring to FIG. 8B, the diagram 850 includes a user device 852 transmitting diagnostic data 871 to a medical application server 856. The data may be transmitted periodically as the user complies with a particular schedule for sharing such data with his or her physician's office or an interested party. As the data is received, the patient record 854 may be updated 872 to reflect the changes since the last record was updated. The application server 856 may identify the risks 873 and update the records 874 based on the threshold values 875 to identify if any present risks are present. For example, the user may have exceeded a blood pressure threshold that would invoke a call, message, appointment with his or her medical treatment facility. Or, the patient may receive an automated prescription adjustment based on the result of the diagnosis or present health condition. The facility server 858 may be notified of the risks 876 so appropriate measures may be taken to correct the health concern. The patient may receive updated instructions 877, such as change your medication to correct this blood pressure elevation. Or, other data that may be reduce the blood pressure by patient compliance (i.e., no salt, walking, relaxing, weight loss, etc.). The patient may be required to acknowledge 878 the advice or information prior to any other action being taken. Ultimately, the medical facility will be notified 879A and any appointments 879B will be sent to the user device 852 and the patient record will be updated accordingly 879C.

Figure 8C:
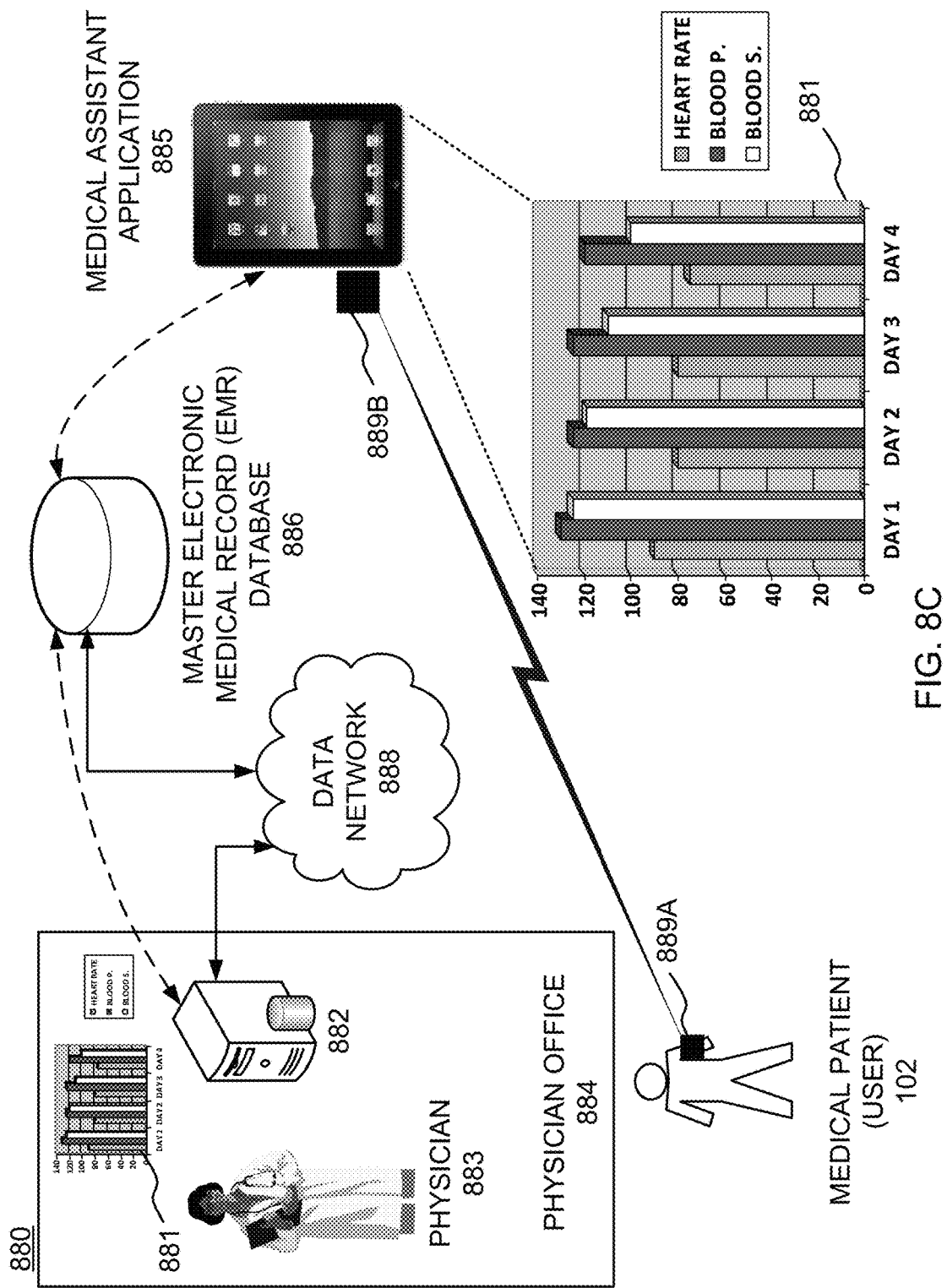
FIG. 8C illustrates an example patient diagnostic communication network according to example embodiments.

FIG. 8C illustrates an example communication network of a patient diagnostic application that monitors and provides assistance to the patient and the patient medical facility. In operation, a patient 102 may have a diagnostic instrument, sensor or other device 889A that is attached to his or her body so health related data 881 can be collected and provided to the user's computing device 885. The application 885 operating on the device may be setup to register the data as a table or report in a master record for the patient 886 that is accessible by the physician office 884 and its corresponding computer server 882 via the data network 888. The diagnostic data 881 can be setup as part of a daily report or an appointment screening report that provides the physician 883 with information pertaining to the user's current health status before or contemporaneous with a present appointment.

Figure 8D:
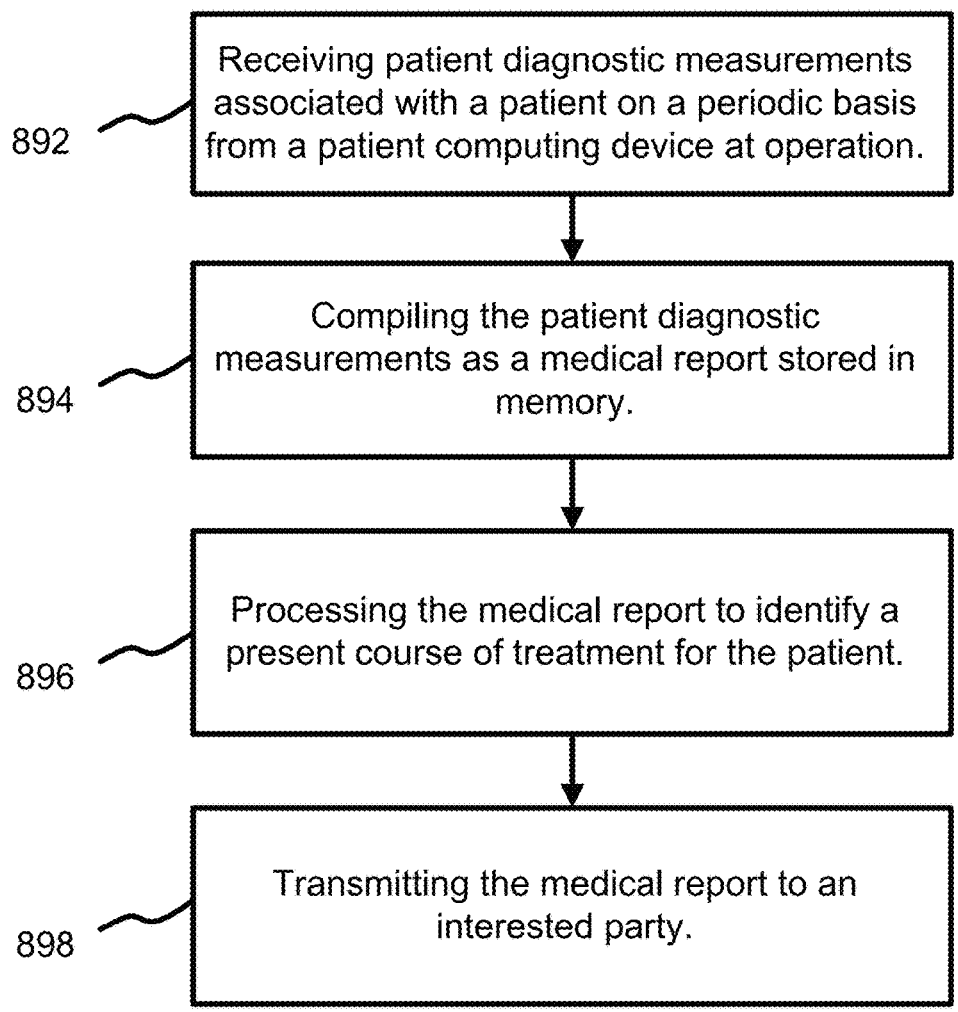
FIG. 8D illustrates an example flow diagram of an example method of operation according to example embodiments.

FIG. 8D illustrates an example of a method of operation according to example embodiments. Referring to FIG. 8D, the method 890 provides receiving patient diagnostic measurements associated with a patient on a periodic basis from a patient computing device at operation 892 and compiling the patient diagnostic measurements as a medical report stored in memory at operation 894. The measurements may be received once an hour, day, etc., however, the reports can be generated to identify the potential problems or highlight the actual measurements which have exceeded the threshold measurements and which are indicative of a health concern. The medical report may then be processed to identify a present course of treatment for the patient at operation 896, and the medical report is transmitted to an interested party at operation 898. The patient is now undergoing a review and may receive information, appointments, emergency services, etc.

In another example, the receiving the patient diagnostic measurements may include receiving blood pressure measurements, blood sugar measurements, heart rate measurements, and breathing pattern measurements. Those measurements are compared with predetermined threshold values, and at least one predetermined threshold value is identified as having been exceeded by the patient diagnostic measurements. Responsive to identifying the predetermined threshold value being exceeded, the course of treatment for the patient may be generated to lower the patient diagnostic measurement which has exceeded the predetermined threshold value. The course of treatment may include information, appointments, medication modifications, emergency assistance.

User diagnostic data may be sent to a medical facility and linked with a present patient visit record associated with the medical facility so at least one present health concern category can be generated based on the medical report. For instance, the patient visit can then be directed by the report instead of undergoing a series of questions in order to arrive at the patient's present condition. Next, a series of notifications can be generated and transmitted to the patient's computing device, which include information associated with the present course of treatment, and the notifications may be transmitted to the patient computing device based on a predetermined time schedule.

Monitoring the patient may be performed to ensure the patient is complying with specific physician instructions, such as taking medications at the proper time, etc., and will, in turn, remain healthy and will not require re-admittance any sooner than anticipated or expected. This also provide assurance that the patient is not doing things they should not be doing (e.g. jogging, driving, etc.) all of those types of activities could be tracked/identified by an accelerometer and logged to trigger a reminder or doctor initiated consultation to reduce further chances of damaging activities.

Figure 9A:
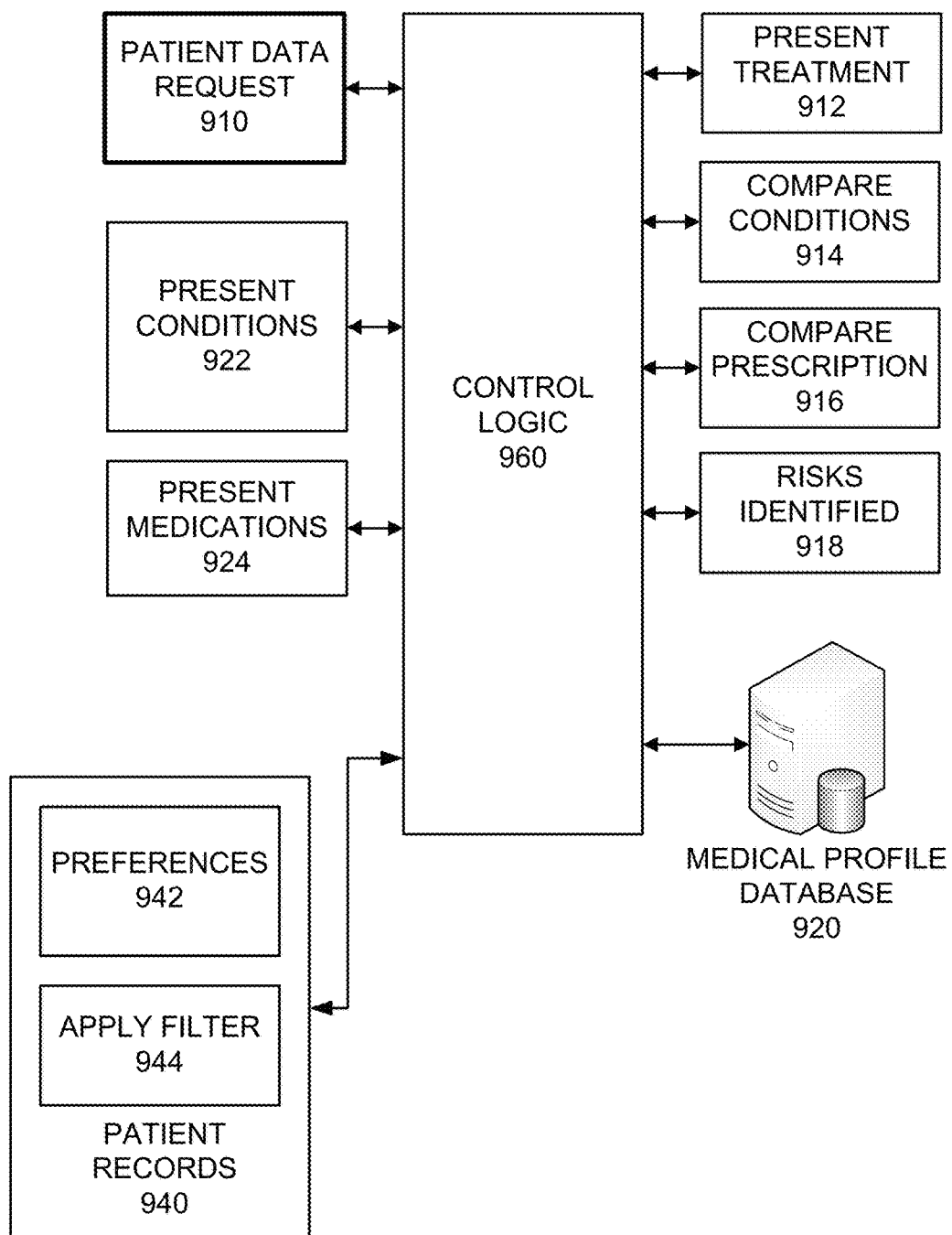
FIG. 9A illustrates an example logic diagram of a patient health monitoring application according to example embodiments of the present application.

According to another example embodiment of the present application, a patient may have his or her medical history readily obtainable via his or her computing device. The information may remain private but can be accessed by a medical service provider (e.g., physician office, hospital, emergency medical services, etc.). FIG. 9A illustrates an example logic diagram of a medical information sharing platform according to example embodiments. Referring to FIG. 9A, the logic 900 includes a control logic processor 960 that receives input, such as a patient data request from a hospital or comparable facility to identify the patient's status and whether he or she can or cannot be associated with a particular course of treatment.

In one example, the patient may be admitted to a hospital in a hurry due to an emergency condition (e.g., collapse, heart attack, severe anxiety condition, severe bleeding, bone break, etc.). The patient may be carrying his or her smartphone device which may have an accessible profile used to access the patient's updated history. The patient may have a near field communication (NFC) antenna system in the device that allows the medical assistant to touch the device and receive a report about the patient's conditions 922, profile, medications 924, allergies, etc. The logic may enable a present treatment 912 plan to be setup by identifying the restrictions or non-restrictions in the report and comparing those to other conditions 914 and prescriptions 916 to identify the risks and whether a particular course of treatment or a treatment plan is acceptable. The information may be updated in a medical profile database 920 and the user's preferences may also be retrieved from the patient records 940 and applied via a filtering function 944.

Figure 9B:
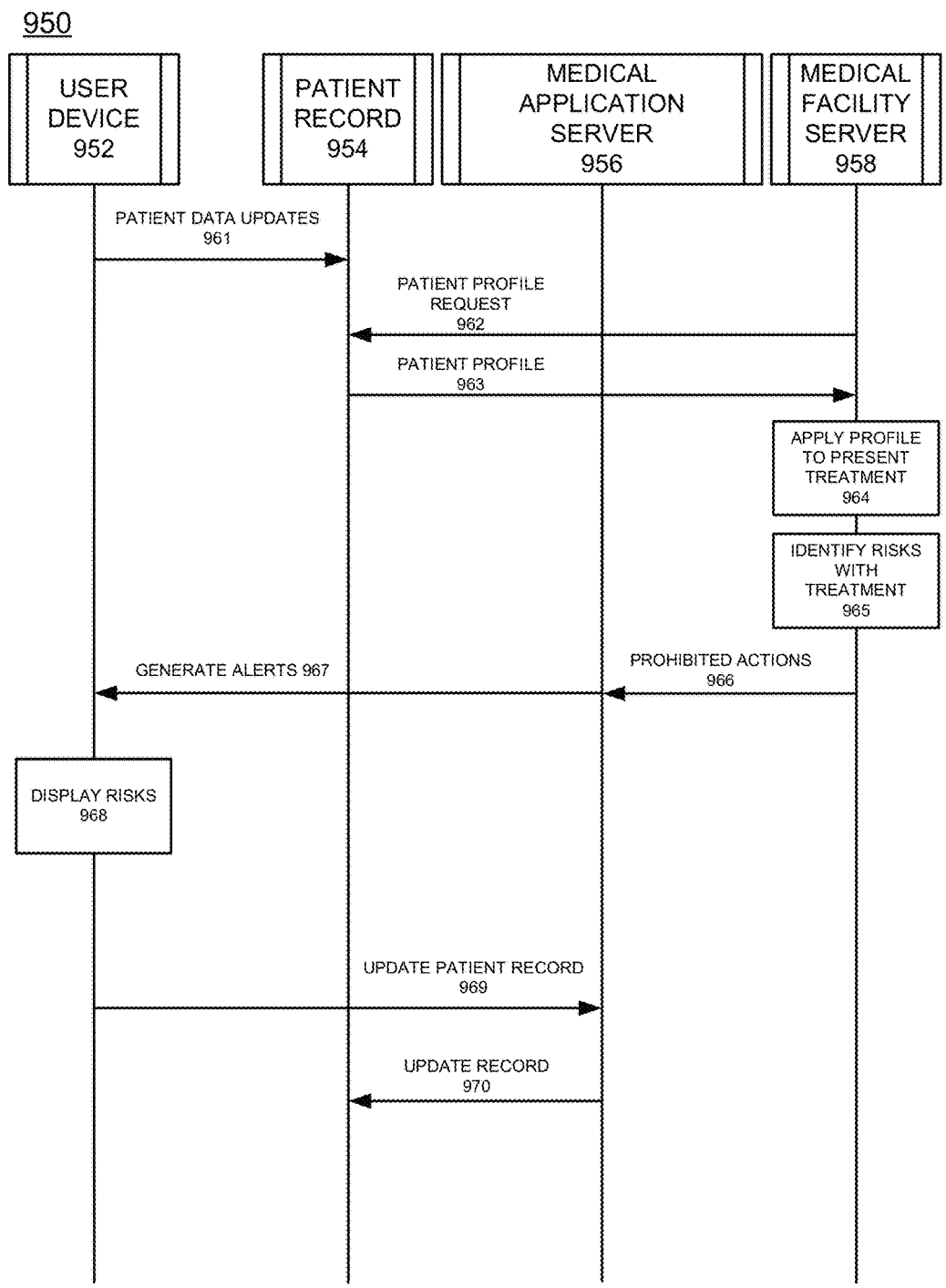
FIG. 9B illustrates a system communication diagram of a patient health monitoring application according to example embodiments.

FIG. 9B illustrates an example of a system signaling diagram of a medical facility scheduling algorithm according to example embodiments. Referring to FIG. 9B, the system diagram includes a user device 952 which offers patient data updates 961 to a patient record 954 as they become available. The medical facility server 958 of the hospital or treatment center may request the data 962 as the patient is admitted and the information may be shared 963 so a patient record can be generated for the present visit. The profile information can then be applied 964 and the risks can be identified 965 and shared with the users so the correct type of treatment can be administered. All the prohibitive actions 966 can be extracted and shared will all interested parties including the user device via an alert 967. This provides the patient and/or the medical assistant with an opportunity to view the concerns right on the patient's smartphone for convenience or in the event the patient is sleeping or unconscious. The risks can be displayed 968 and the patient records may be updated 969 at the application server 956 so the patient record 970 can include the most recent changes and actions.

Figure 9C:
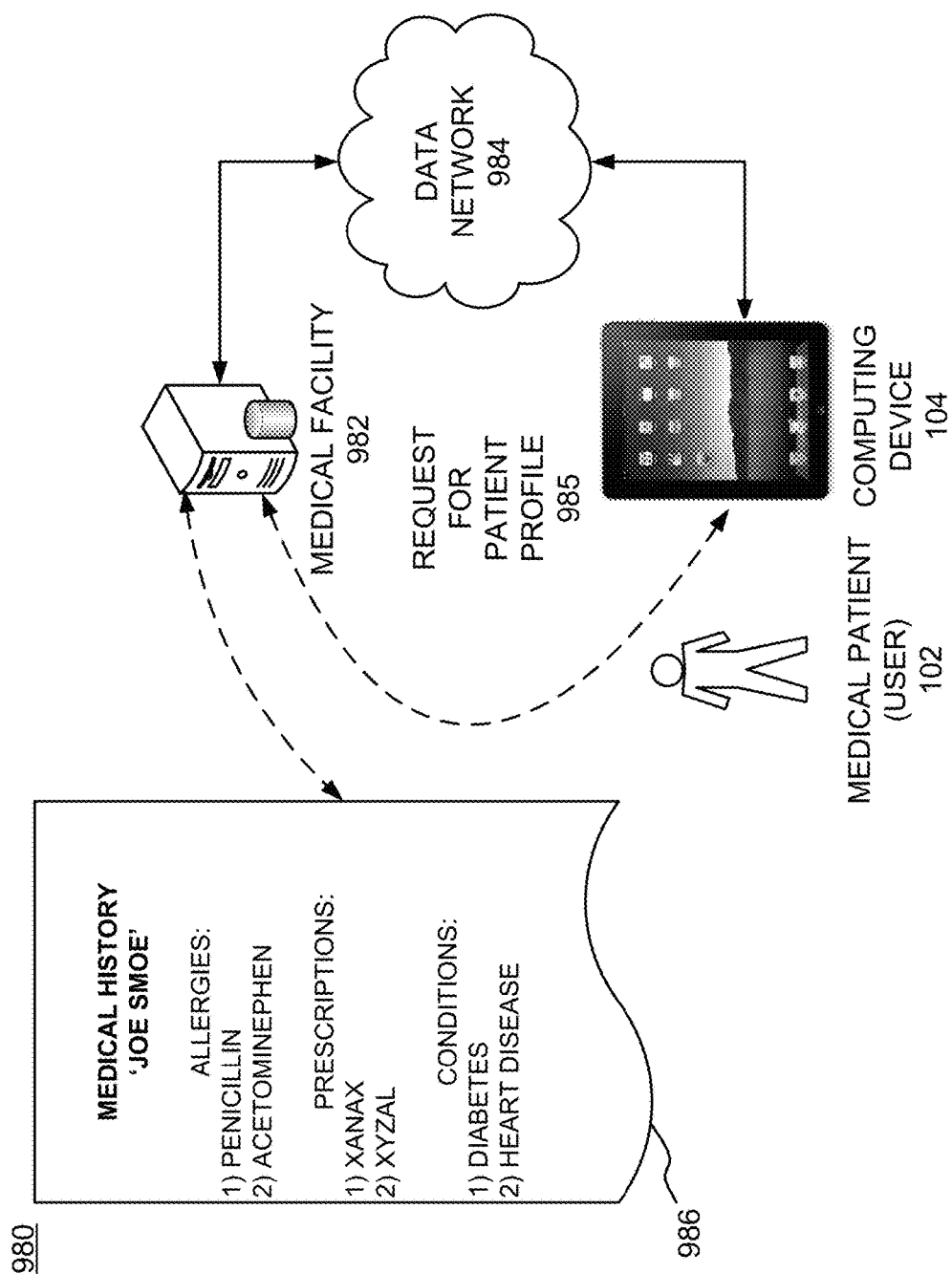
FIG. 9C illustrates an example patient information sharing communication network according to example embodiments.

FIG. 9C illustrates an example network diagram of a user medical condition sharing scenario according to example embodiments. Referring to FIG. 9C, the network 980 includes a medical patient 102 operating a computing device 104. The medical facility 982 may request the patient profile 985 and share the information across a data network 984 to the patient's medical record, insurance company or other interested third parties. The information may provide a basis format of the patient's medical history 986 including conditions, current prescriptions, allergies, etc. The information may be accessible via a simple NFC touch example or via a SMS message notification or other communication message. The facility may receive the information and setup a treatment plan based on those known conditions being experienced by the patient 102.

Figure 9D:
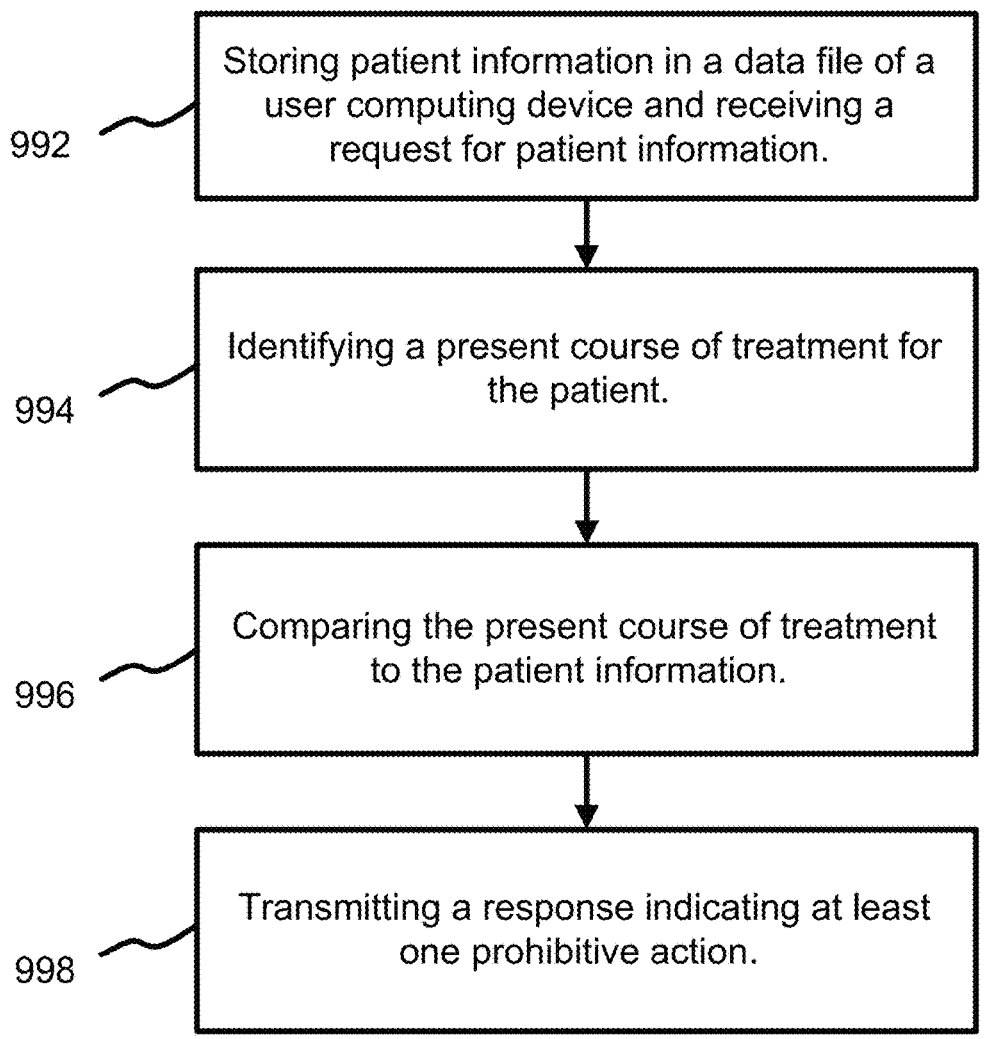
FIG. 9D illustrates an example flow diagram of an example method of operation according to example embodiments.

FIG. 9D illustrates an example method of operation according to example embodiments. Referring to FIG. 9D, the method 990 may include storing patient information in a data file of a user computing device at operation 992 and receiving a request for patient information. The method may also include identifying a present course of treatment for the patient at operation 994 and comparing the present course of treatment to the patient information at operation 996. The comparing operation could prevent undesirable or dangerous results from occurring since the patient's information is readily shared and available for medical assistant or physician to view and apply. The method may also include transmitting a response indicating at least one prohibitive action to the application so the course of treatment can be modified or customized based on the identified restriction.

In addition, the method may also include identifying present medications being administrated to the patient which are stored in the data file, and comparing the present medication to the present course of treatment to identify a predetermined prohibitive action based on the present medication being combined with the present course of treatment. Also, an alert can be generated to inform a user of the computing device of the predetermined prohibitive action. Furthermore, a present medical condition can be identified and associated with the patient and stored in the data file, and the present medical condition is then compared to the present course of treatment. A predetermined prohibitive action can be identified based on the present medical condition being combined with the present course of treatment, and an alert to inform a user of the computing device of the predetermined prohibitive action can be generated.

In another example, an information sharing session may be initiated via a user computing device responsive to an information sharing action, and the patient information can be uploaded to a medical facility upon receiving the information sharing action. Next, a current medical profile can be created for the user of the user computing device based on the uploaded patient information and the present course of action. In one example, the present course of treatment may be a new medication, a surgical procedure and/or a medical procedure. When attempting to receive the user data, a near field communication (NFC) session initiation may be performed with the user communication device via a touch interaction or other communication initiation, and the patient information can then be received responsive to the NFC session being initiated. An alternative course of action may be created responsive to the predetermined prohibitive action.

Extracting patient data could be performed by the patient's history being sent electronically via a secure connection, between the patient's mobile phone and the facility. In this case, the patient's history/medical record would be stored on their mobile device or in a personal record stored in the "cloud" so that if such data is ever compromised or stolen, the mobile station itself would not have any valuable medical data accessible in memory. The information would normally be sent from the patient's personal cloud files to the facility.

In a similar approach, the patient's information would be regularly uploaded to their personal cloud source on an ongoing basis and then shared with the facility on a regular ongoing basis at specified durations/times of the patient's choice (e.g. once a month, etc.) In this way, there is a regular flow of information rather than having to do a one-time upload each visit which could introduce other operational issues. The patient's history might also be able provided to the facility by using a simple portable computer drive/ memory device. The patient's information might also be stored on/inside a "wearable device" which could then transmit information directly to the facility's database.

Figure 10:
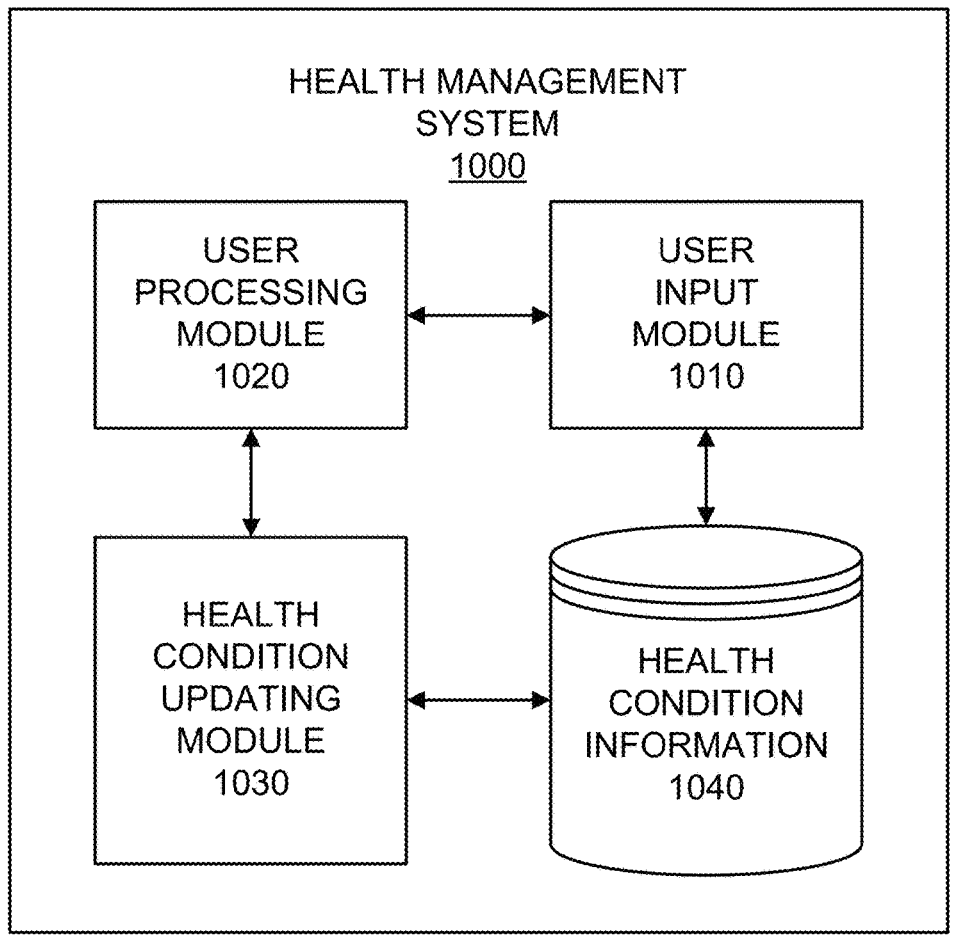
FIG. 10 illustrates an example system configuration according to example embodiments.

FIG. 10 illustrates an example health management system 1000 which may be used a single entity, multiple entities or a combination of hardware and/or software modules. The modules may include a user input module 1010 that receives the input from a particular user to update a user's objective or profile. The processing module 1020 may receive input and determine an outcome or action. The health condition processing module 1030 may be used to identify the patient's current health conditions and whether to store that information in memory 1040, share the information or modify the information accordingly.

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example FIG. 11 illustrates an example network element 1100, which may represent any of the above-described network components.

Figure 11:
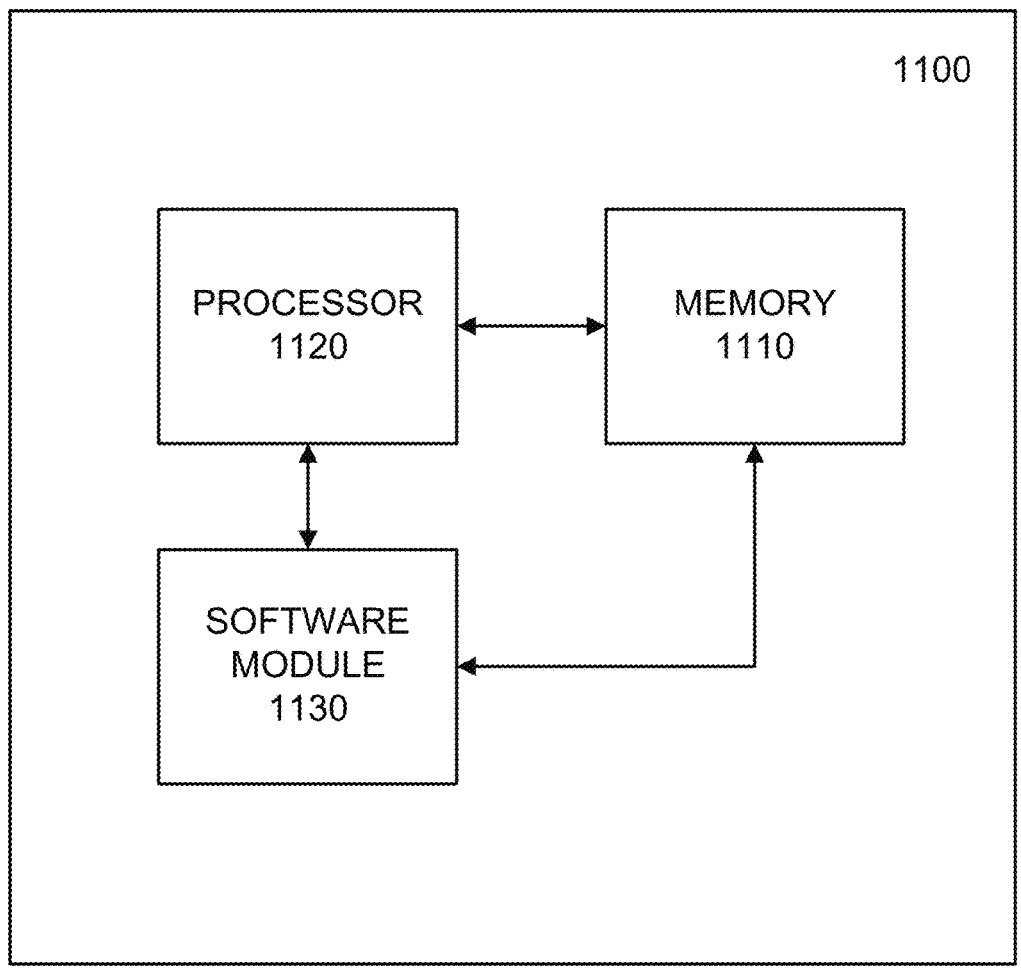
FIG. 11 illustrates an example network entity device configured to store instructions, software, and corresponding hardware for executing the same, according to example embodiments of the present application.

As illustrated in FIG. 11, a memory 1110 and a processor 1120 may be discrete components of the network entity 1100 that are used to execute an application or set of operations. The application may be coded in software in a computer language understood by the processor 1120, and stored in a computer readable medium, such as, the memory 1110. The computer readable medium may be a non-transitory computer readable medium that includes tangible hardware components in addition to software stored in memory. Furthermore, a software module 1130 may be another discrete entity that is part of the network entity 1100, and which contains software instructions that may be executed by the processor 1120. In addition to the above noted components of the network entity 1100, the network entity 1100 may also have a transmitter and receiver pair configured to receive and transmit communication signals (not shown).

Although an exemplary embodiment of the system, method, and computer readable medium of the present application has been illustrated in the accompanied drawings and described in the foregoing detailed description, it will be understood that the application is not limited to the embodiments disclosed, but is capable of numerous rearrangements, modifications, and substitutions without departing from the spirit or scope of the application as set forth and defined by the following claims. For example, the capabilities of the system of FIG. 10 can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way, but is intended to provide one example of many embodiments of the present application. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed, but is merely representative of selected embodiments of the application.

One having ordinary skill in the art will readily understand that the application as discussed above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent, while remaining within the spirit and scope of the application. In order to determine the metes and bounds of the application, therefore, reference should be made to the appended claims.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method comprising:
receiving, via a user interface, at least one user inquiry including at least one user preference;
illustrating, via the user interface, the at least one user inquiry via an input parameter and a snapshot;
receiving a request to schedule an appointment at a medical facility;
identifying a user account associated with the request and the user's medical history;
identifying the user account as having a delinquent compliance score;
scheduling the appointment in a delinquent appointment time slot;
receiving confirmation the appointment occurred;
updating the user's medical record to indicate the appointment occurred and to increase the user's compliance score;
receiving a confirmation message that the user account has achieved a nominal rating;
increasing the user's compliance score above a predetermined threshold;
transmitting an update message to the user device to inform of the compliance score increase and to offer a new scheduling opportunity;
applying the at least one user preference to a scheduling algorithm;
automatically establishing a new appointment based on the at least one user preference; and
transmitting a time of the new appointment to the user interface for confirmation.

2. The method of claim 1, wherein the scheduling the appointment in the delinquent appointment time slot comprises identifying a partial time slot between two established regular time slots, and transmitting an option to the user device to schedule the appointment in the partial time slot.

3. The method of claim 2, further comprising:
creating the appointment based on the user device selection received.

4. The method of claim 1, further comprising:
receiving a new scheduling request from the user device; and
scheduling a new appointment in a regular time slot responsive to receiving the new scheduling request.

5. The method of claim 1, further comprising:
identifying a severe medical condition from user's medical history;
overriding the delinquent compliance score; and
scheduling the appointment in a normal appointment time slot.

6. An apparatus, comprising:
a receiver configured to receive, via a user interface, at least one user inquiry including at least one user preference, and to receive a request to schedule an appointment at a medical facility;
a processor configured to
illustrate, via the user interface, the at least one user inquiry via an input parameter and a snapshot;
identify a user account associated with the request and the user's medical history,
identify the user account as having a delinquent compliance score, and
schedule the appointment in a delinquent appointment time slot,
the receiver is further configured to receive confirmation the appointment occurred; and
the processor is further configured to update the user's medical record to indicate the appointment occurred and to increase the user's compliance score;
wherein the receiver is further configured to receive a confirmation message that the user account has achieved a nominal rating,
the processor is further configured to increase the user's compliance score above a predetermined threshold and to apply the at least one user preference to a scheduling algorithm, and automatically establish a new appointment based on the at least one user preference; and
a transmitter configured to transmit an update message to the user device to inform of the compliance score increase and to offer a new scheduling opportunity and to transmit a time of the new appointment to the user interface for confirmation.

7. The apparatus of claim 6, wherein the appointment being scheduled in the delinquent appointment time slot comprises the processor being configured to identify a partial time slot between two established regular time slots, and
the transmitter is configured to transmit an option to the user device to schedule an appointment in the partial time slot.

8. The apparatus of claim 7, wherein the processor is further configured to create the appointment based on the user device selection received.

9. The apparatus of claim 6, wherein the receiver is further configured to receive a new scheduling request from the user device, and the processor is further configured to schedule a new appointment in a regular time slot responsive to receiving the new scheduling request.

10. The apparatus of claim 6, wherein the processor is further configured to identify a severe medical condition from user's medical history, override the delinquent compliance score, and schedule the appointment in a normal appointment time slot.

11. A non-transitory computer readable storage medium configured to store instructions that when executed cause a processor to perform:
receiving, via a user interface, at least one user inquiry including at least one user preference;
illustrating, via the user interface, the at least one user inquiry via an input parameter and a snapshot;
receiving a request to schedule an appointment at a medical facility;
identifying a user account associated with the request and the user's medical history;
identifying the user account as having a delinquent compliance score;
scheduling the appointment in a delinquent appointment time slot;
receiving confirmation the appointment occurred;
updating the user's medical record to indicate the appointment occurred and to increase the user's compliance score;
receiving a confirmation message that the user account has achieved a nominal rating;
increasing the user's compliance score above a predetermined threshold; and
transmitting an update message to the user device to inform of the compliance score increase and to offer a new scheduling opportunity;
applying the at least one user preference to a scheduling algorithm;
automatically establishing a new appointment based on the at least one user preference; and transmitting a time of the new appointment to the user interface for confirmation.

12. The non-transitory computer readable storage medium of claim 11, wherein the scheduling the appointment in the delinquent appointment time slot comprises identifying a partial time slot between two established regular time slots, and transmitting an option to the user device to schedule the appointment in the partial time slot.

13. The non-transitory computer readable storage medium of claim 12, wherein the processor is further configured to perform:

creating the appointment based on the user device selection received.

14. The non-transitory computer readable storage medium of claim 11, wherein the processor is further configured to perform:

receiving a new scheduling request from the user device; and scheduling a new appointment in a regular time slot responsive to receiving the new scheduling request.

* * * * *